(12) United States Patent
Lerner et al.

(10) Patent No.: US 6,678,553 B2
(45) Date of Patent: *Jan. 13, 2004

(54) DEVICE FOR ENHANCED DELIVERY OF BIOLOGICALLY ACTIVE SUBSTANCES AND COMPOUNDS IN AN ORGANISM

(75) Inventors: Eduard N. Lerner, Amsterdam (NL); Leonid Lerner, Los Angeles, CA (US)

(73) Assignee: Intraabrain International NV, Curacao (AN)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 65 days.

(21) Appl. No.: 09/077,123

(22) PCT Filed: Nov. 19, 1996

(86) PCT No.: PCT/EP96/05086

§ 371 (c)(1),
(2), (4) Date: May 20, 1998

(87) PCT Pub. No.: WO97/18855

PCT Pub. Date: May 29, 1997

(65) Prior Publication Data

US 2002/0123678 A1 Sep. 5, 2002

(30) Foreign Application Priority Data

Nov. 21, 1995 (EP) ............................................ 95203173
Dec. 22, 1995 (EP) ............................................ 65203601
Oct. 22, 1996 (EP) ............................................ 96200081
Oct. 22, 1996 (EP) ............................................ 96200082

(51) Int. Cl.[7] ................................................. A61N 1/30

(52) U.S. Cl. ...................... 604/20; 604/501; 604/93.01; 600/380

(58) Field of Search ............................. 604/20–22, 504, 604/514, 70, 19, 48, 500, 501, 290, 294, 93.01; 600/372, 380, 382, 383, 554, 378; 607/1, 2, 3, 35, 45, 96, 98, 99, 100, 101, 104, 105, 108, 109, 113, 115, 120, 135

(56) References Cited

U.S. PATENT DOCUMENTS

| | | | | |
|---|---|---|---|---|
| 5,084,006 A | * | 1/1992 | Lew et al. | 604/20 |
| 5,215,520 A | * | 6/1993 | Shroot et al. | 604/20 |
| 5,298,017 A | * | 3/1994 | Theeuwes et al. | 604/20 |
| 5,505,700 A | * | 4/1996 | Leone et al. | 604/96 |
| 5,807,306 A | * | 9/1998 | Shapland et al. | 604/21 |
| 5,843,016 A | * | 12/1998 | Lugnani et al. | 604/21 |
| 6,001,088 A | * | 12/1999 | Roberts et al. | 604/501 |

FOREIGN PATENT DOCUMENTS

| | | | | |
|---|---|---|---|---|
| AU | WO-96/16693 A1 | * | 6/1996 | 604/20 |
| WO | WO 91/16945 | * | 11/1991 | 604/21 |

* cited by examiner

*Primary Examiner*—Manuel Mendez
*Assistant Examiner*—Jennifer Maynard
(74) *Attorney, Agent, or Firm*—Nixon & Vanderhye P.C.

(57) ABSTRACT

A device and methods are described for a non-invasive transnasal and transocular drug delivery to the central nervous system using iontophoresis technology. By delivered through the olfactory nerve and the optical nerve, a biologically active substance of interest can be enhanced to be delivered into the CNS and CSF and bypassing the blood-brain barrier. Such drug delivery system can also be enhanced by using phonophoresis and other enhancement techniques.

20 Claims, 8 Drawing Sheets

DEVICE FOR ENHANCED DELIVERY OF BIOLOGICALLY ACTIVE SUBSTANCES AND COMPOUNDS IN AN ORGANISM

BACKGROUND OF THE INVENTION

1. INTRODUCTION

Most of the efforts currently under way to discover new therapeutic drugs for disorders of the central nervous system (CNS) will also face the problem of delivering them to the brain without impairing the activity or integrity of such substances or compounds, while minimizing systemic adverse effects. And that means finding a way around—or through—the blood brain barrier (BBB), a physiological barrier between bloodstream and brain.

A National Institutes of Mental Health (NIMH) study showed that, in the United States, one out of three individuals suffers from a CNS disorder at some time in life. Approximately two million in the same country have suffered a stroke, which is the third leading cause of death in the United States.

2. IONTOPHORESIS

After the discovery of the electrical nature of nerve impulse by Galvani in 1791, attention focused on the possibility of using electricity as a mode of drug delivery. It has been long known that medicines could be introduced into the human body by way of the skin. The skin has a selective permeability to lipophilic (lipid soluble) substances and acts as a barrier to hydrophilic (water soluble) substances. In 1747, Veratti suggested that hydrophobic drugs might be Introduced to the subcutaneous tissue through human skin by the application of a direct current. This mode has become known as iontophoresis (meaning ion transfer).

In Table 1 we present several examples of drugs introduced through the skin by iontophoresis for some conditions.

| Drug | condition |
| --- | --- |
| Acetic acid | Myositis ossificans |
| Aspirin | Rheumatic disease |
| Dexamethasone and lidocaine | Tendinitis, bursitis, rheumatoid arthritis |
| Diclofenac sodium | Scapula-humoral periarthritis, elbow epicondylitis |
| Iodine | Fibrosis, adhesions, scar tissue, trigger finger |
| lidocaine | local anesthesia |
| Morphine | Post-operative analgesia |
| Pilocarpine | Sweat test (cystic fibrosis) |
| Pirprophene | Rheumatic diseases |
| Potassium citrate | Rheumatoid arthritis |
| Potassium iodide | Scar tissue |
| Silver | Chronic osteomyelitis |
| Salicylate | Plantar warts, scar tissue |
| Sodium fluoride | Tooth hypersensitivity |

Table 1: Drugs introduced by iontophoresis for corresponding conditions, substances that can be introduced by iontophoresis.

This is only a small part of different drugs or biologically active substances that can be introduced by iontophoresis. Many lipophilic drugs, such as scopolamine for motion sickness, clonidine for hypertension, and nitroglycerin for the treatment of angina pectoris, can be readily delivered through human skin. With these drugs, the concentration gradient between the drug-loaded reservoir and the body is sufficient enough to deliver the drug through the skin at therapeutic dosage rates. However, this is not the case for hydrophilic drugs.

Because topical application fails to deliver therapeutic dosages of hydrophilic drugs, traditional methods, such as oral or parenteral systemic drug administration, have been favored. However, these methods have several disadvantages.

First, systemic administration may lead to massive inactivation of a drug as a result of the enzymatic action of the liver. Also, oral administration may give rise to incomplete or erratic absorption due to factors like food interaction, inactivation in the gastro-intestinal tract, disease status, and concomitant medication. Furthermore, oral drug administration may give rise to fluctuations in the concentration of a drug in the systemic circulation. This may in turn result in toxic or sub-therapeutic blood levels of the drug.

These problems have been and still are the subject of extensive research and can only partly be dealt with in most cases using different methods including oral administration of pro-drugs and controlled release dosage forms. However, these problems may also be avoided by the use of iontophoresis. Using electric current as an external driving force, hydrophilic, charged drugs can be readily introduced through the epidermal level.

Various types of drugs are potential candidates for iontophoresis. Hydrophilic, charged drugs with relatively low molecular weight are the most suitable for the procedure, although the delivery of some large peptides and hormones by this technique has also proven to be successful.

Direct current, or galvanic current, is the current of choice for iontophoresis. Direct current allows the maximum ion transfer per unit of applied current, because its course is uninterrupted.

According to ohm's law: $V=IR$, where V is voltage, I is current, and R is resistance, the voltage generated within the system is therefore dependent on the resistance of the skin or other tissue during the treatment.

It has been suggested by many investigators that penetration of hydrophilic, charged substances occurs mainly by way of sweat ducts, sebaceous glands, and hair follicles and imperfection of the skin (The Shunt Pathway theory).

According to the flip-flop gate mechanism, it has been suggested that permeability of skin may be altered as a result of the application of an electric potential across the skin. Jung et al. in 1983 found that the only structural requirement for pore formation was the presence of alpha-helical polypeptides. When an electric potential is applied across a physiological membrane, a voltage-dependent "flip-flop,' of the helices occurs. The skin permeability can be enhanced by the formation of "artificial shunts" by the use of direct current as applied during iontophoresis.

The following factors affect iontophoretic skin permeation:
- molecular weight,
- current density,
- skin impedance,
- ion conductivity,
- pH of the drug solution,
- ion valence,
- duration of lontophoresis,
- concentration of the drug ion in the solution.

In optimal conditions, an organism receives only 10% of the substance on the electrode applied to the skin. In fact, an organism may receive from 1 to 10% of the substance.

Therapeutically, a current density of less than 1 mA per square inch of electrode surface is recommended.

According to Faraday's, First Law of Electrolysis, which states that the mass of a substance liberated at (or dissolved from) an electrode during electrolysis is directly proportional to the quantity of electrolyte.

An electrolyte can be defined as a substance that conducts electric current as a result of dissociation into positively and negatively charged particles called ions, which migrate toward and ordinarily are discharged at the negative and positive electrodes (cathode and anode respectively), of an electric circuit. The most familiar electrolytes are acids, bases, and salts, which ionize when dissolved in such polar solvents as water or alcohol. An essential requirement for solvents to be used is that they conduct electric current and have to possess an electric dipole.

Polar solvents consist of strong dipolar molecules having hydrogen bonding. Water is a very unique polar solvent in that it also has a high dielectric constant, which indicates the effect that a substance has, when it acts as a medium, on the ease with which two oppositely charged ions may be separated. The higher the dielectric constant of a medium, the easier it is to separate two oppositely charged species in that medium, which is an essential requirement for the existence of ionized molecules that may be moved by an electric current, as with iontophoresis.

Table 2 shows some useful polar solvents with their dielectric constants. The values listed are relative to a vacuum which by definition has a dielectric constant of unity.

| Solvent | Dielectric constant ($\epsilon$ at 20° C.) |
| --- | --- |
| water | 80 |
| glycerin | 46 |
| ethylene glycol | 41 |
| methyl alcohol | 33 |
| ethyl alcohol | 25 |
| n-propyl alcohol | 22 |

The degree of dissolution and subsequent ionization can be improved and regulated by means of the addition of suitable electrolytes forming buffer systems in the selected polar solvent or mixtures thereof.

Siddiqui et al. found that during passive absorption the penetration rate of lidocaine was greatest at the higher pH levels (9.4 and 11.7), where lidocaine is mainly non ionized. On the other hand, lidocaine is mainly in the ionized form at pH 3.4 and 5.2.

During transdermal iontophoresis, drugs do not penetrate to a big depth. After applying a current of 5 mA to the right side and 0 mA to the left side for 20 minutes, radiolabeled Dexamethasone was detected to a maximal depth of 1.7 cm in the right side, which was the location of the hip joint capsule of the monkey (Glass et al).

For electrophoresis, not only direct (galvanic) current can be used, but other different impulse currents as well of both direct polarity and alternating polarity in a rectified regime (diadinamic, sinusoidal, fluctuating, etc.).

It is possible to use or to combine different types of energy. For example, we can combine iontophoresis with ultrasound, magnetic field, temperature-increase, etc.

When choosing a polarity, it is necessary to take into account that ions of all the metals, local anesthetic drugs, most alkaloids, and antibiotics have all a positive charge at physiological pH. Therefore, they must be introduced from an anode. On the other hand, ions of all the metalloids and acid radicals have all a negative charge at a physiological pH, and must be introduced from a cathode. There have been a series of interesting results proving a successful local introduction of drugs and other chemical substances into animal brains by means of micro-iontophoresis.

3. PHARMACOKINETICS

3.1 Physicochemical Factors in Transfer of Drugs Across Membranes

The absorption, distribution, biotransformation, and excretion of a drug all involve its passage across cell membranes. Important characteristics of a drug are its molecular size and shape degree of ionization, and relative lipid solubility of its ionized and non ionized forms.

Passive Processes

Drugs cross membranes by either passive processes or by mechanisms involving the participation of components of the membrane. Both non-polar lipid-soluble compounds and polar water-soluble substances that retain sufficient lipid solubility can cross the lipid portion of the membrane by passive diffusion. Such transfer is directly proportional to the concentration gradient across the membrane. The greater the partition coefficient, the higher the concentration of drug in the membrane and the faster is its diffusion. Bulk flow of water carries with it any water-soluble molecule that is small enough to pass through the channels. Filtration is a common mechanism for transfer of many small, water-soluble, polar and non-polar substances.

Capillary endothelial cells have large channels (40 Å) and molecules as large as albumin may pass to a limited extent from the plasma to the extracellular fluid. In contrast, the channels in the intestinal epithelium and most cell membranes are about 4 Å in diameter and permit passage only of water, urea, and other small, water-soluble molecules. Substances generally do not pass through channels in cell membranes if their molecular mass is greater than 100 to 200. Most inorganic ions are sufficiently small to penetrate the channels in membranes, but their concentration gradient across the cell membrane is generally determined by the transmembrane potential.

Weak Acids and Bases and Influence of pH.

Most drugs are weak acids or bases and are present in solution as both the non-ionized and ionized species. The non-ionized portion is usually lipid soluble and can readily diffuse across the cell membrane. In contrast, the ionized fraction is often unable to penetrate the lipoid membrane because of its low lipid solubility, or to pass the membrane channels because of its size. If the ionized portion of a weak electrolyte can pass through the channels, or through the membrane, it will distribute according to the transmembrane potential in the same manner as an inorganic ion.

Carrier-mediated Active Membrane Transport

Passive processes do not explain the passage of all drugs across cell membranes. Active transport is responsible for the rapid transfer of many organic acids and bases across the renal tubule, choroid plexus, and hepatic cells. The transported substance is transferred against an electrochemical gradient.

Transcellular fluxes are formed by the active transport of $Na^+$ across epithelial cells. Proteins and other macromolecules slowly cross epithelial cells by pinocytosis, a form of vesicular transport.

3.2 Absorbtion of Drugs

It is of practical importance to know the manner in which drugs are absorbed. The rate of absorption influences the time course of drug effect, and it is an important factor in determining drug dosage. In addition, choice of the route by which a drug is administered is often influenced by considerations of drug absorption.

Factors That Modify Absorption.

Absorption from all sites of administration is dependent upon drug solubility. Drugs given in aqueous solution are more rapidly absorbed than those given in oily solution, suspension, or solid form. For those given in solid form, the rate of dissolution may be the limiting factor in their absorption. Local conditions at the site of absorption alter solubility. The concentration of a drug influences its rate of absorption.

Drugs ingested or injected in solutions of high concentration are absorbed more rapidly than are drugs in solutions of low concentration. The circulation to the site of absorption also affects drug absorption. Increased blood flow, brought about by massage or local application of heat, enhances absorption of a drug. The area of the absorbing surface to which a drug is exposed is one of the more important determinants of the rate of drug absorption. Often there is a choice of the route by which a therapeutic agent may be given, and a knowledge of the advantages and disadvantages of the different routes of administration is then of primary importance. Oral ingestion is the most ancient method of drug administration. Disadvantages to the oral route include emesis as a result of irritation to the gastrointestinal mucosa, destruction of some drugs by digestive enzymes or low gastric pH, and formation of complexes with food components that cannot be absorbed. Drugs absorbed from the gastrointestinal tract may be extensively metabolized by the liver before they gain access to the general circulation. The parenteral injection of drugs has certain distinct advantages over oral administration. In some instances, parenteral administration is essential for the drug to be absorbed in its active form. Absorption is usually more rapid and more predictable than when a drug is given by mouth. Injection of drugs also has its disadvantages. Strict asepsis must be maintained to avoid infection, an intravascular injection may occur when it is not intended, pain may accompany the injection, and it is often difficult for a patient to perform the injection himself. Parenteral therapy is also more expensive and less safe than oral medication.

Intrathecal Administration

The blood-brain barrier and the blood-cerebrospinal fluid barrier often preclude or slow the entrance of drugs into the CNS. Therefore, when local and rapid effects of drugs on the meninges or cerebrospinal axis are desired, as in spinal anesthesia or acute CNS infections, drugs are sometimes injected directly into the spinal subarachnoid space.

4. The BLOOD-BRAIN BARRIER

It has long been known that the bulk of the brain and the spinal cord is surrounded by a specially secreted clear fluid called the cerebrospinal fluid (CSF). Chemical substances such as metabolites move relatively freely from the alimentary canal into the blood, but not into the CSF. As a result, the blood levels of sugars, amino acids or fatty acids fluctuate over wide range while their concentrations in the CSF remain relatively stable. The same is true for hormones, antibodies, certain electrolytes, and a variety of drugs. Injected directly into the blood they act rapidly on peripheral tissues such as the muscles, heart, or glands but they have little or no effect on the central nervous system (CNS).

When administered into the CSF, however, the same substances exert a prompt and strong action. The conclusion is that the substances injected into the blood do not reach the CSF and the brain with sufficient rapidity and in an effective concentration.

The way in which the brain keeps its environment constant is frequently discussed in terms of a blood-brain barrier (BBB). Once substances have found their way into the CSF, they are free to diffuse into the tissues of the brain. The entry of hydrophilic and relatively large molecules into the CNS is restricted by the existence of a BBB. The BBB separates the brain from the blood circulation and is involved in the homeostasis of the brain. The BBB is situated in the brain microvessels and is composed of various cell types like endothelial cells, astrocytes, microglial cells, perivascular macrophages, and pericytes. The cerebral and endothelial cells form the morphological and functional basis of the BBB.

5. NASAL CAVITY AND OLFACTORY REGION

Internal Nose

On each side of the nose are anterior and posterior openings called the nares. The posterior nares are also called the choanae. The vestibule is the anterior, skin-lined part of the nasal cavity. The nasal septum divides the nose into the two fossae. The lateral wall of the nose is a complicated area anatomically. There are four nasal turbinates, or conchae. Named from below upward, they are the inferior, middle, superior and supreme turbinates. The mucous membrane of the inferior turbinate is very rich in blood vessels and is semi-erectile. The several nasal meatuses are named according to the turbinates that overlie them.

Above the superior and supreme turbinates is the sphenoethmoidal recess, into which the sphenoidal sinus opens. Under the mucosa of the lateral wall of the inferior meatus are large blood vessels (sphenopalatine branches).

Both the external and the internal carotid systems provide a blood supply to the nose. The venous drainage is important because part of it, through the angular vein, leads to the inferior ophthalmic vein and eventually to the cavernous sinus. Most of the venous drainage, however is downward through the anterior facial vein.

Lymphatic Drainage of the Nose is Extensive and Parallels the Venous Drainage.

The olfactory area is located high in the nasal vault above the superior turbinate. Sensory hairs extend from the surface of the olfactory area to the cells that lie deep in the mucosa.

Nerve fibers subserving the sense of smell have their cells of origin in the mucous membrane of the upper and posterior parts of the nasal cavity. The entire olfactory mucosa covers an area of about 2.5 cm2. The central processes of olfactory fila are very fine unmyelinated fibers that converge to form small fascicles enwrapped by Schwann cells and pass through openings in the cribriform plate of the ethmoid bone into the olfactory bulb. The axons of the mitral and tufted enter the olfactory tract, which courses along the olfactory groove of the cribriform plate to the cerebrum. Some fibers project to the medial dorsal nucleus of the thalamus and the hypothalamus. That olfactory stimuli and emotional stimuli are strongly linked is not surprising, in view of their common roots in the limbic system.

According to Bell, the olfactory system has direct neuroanatomical and neurophysiological input to the amygdala and eventually hippocampus. Therefore it is conceivable that chemical stimuli at low levels could trigger limbic dysfunction in patients who happen to meet descriptive criteria for somatization disorder. It is also stated that there is no blood-brain barrier in the nasal passages. The limbic structure (e.g. the amygdala, olfactory bulb and hippocampus) can become easily kindled. The olfactory nerves can transport toxins directly to the limbic system. This may result in symptoms including memory loss, irritable bowel, and migraine headaches.

It has been suggested by Shipley, that it is possible to transport substances which come into contact with the nasal epithelium to the brain and that it is thus possible to influence the function of neurons in the brain, including some which have extensive projection to wide areas of the CNS.

6. THE OPTIC NERVE

The optic nerve, mediating vision, is distributed to the eyeball. Most of its fibers are afferent and originate in the nerve cells of the ganglionic layer of the retina. Developmentally, the optic nerves and the retinae are parts of the brain and their fibers with glia.

The optic nerve, about 4 cm long, is directed backwards and medially through the posterior part of the orbital cavity. It then runs through the optic canal into cranial cavity and joins the optic chiasma. The optic nerve is enclosed in three sheaths, which are continuous with the membranes of the brain, and are prolonged as far as the back of the eyeball. Therefore, there is a direct connection between the optic nerve and the brain structures.

Itaya and van Hoesen described transneuronal retrograde labeling of neurons in the stratum griseum superficiale of the superior colliculus following intraocular injection of wheat germ agglutinin-horseradish peroxidase. A study of the distribution of wheat germ agglutinin-horseradish peroxidase in the visual system following intraocular injections in the chick, rat and monkey confirmed early findings of transneural transport of this conjugate in vivo.

From the overview of the literature given above we can conclude the following. Many substances such as metabolic products, drugs, and other substances cannot or only to a limited extent cross the BBB from the blood into the brain. From the nasal cavity these substances can penetrate into the brain because in the area of 2.5 cm2 of the upper posterior part of the nasal cavity, the BBB does not exist. Therefore, substances introduced into the upper part of the nasal cavity can directly enter the brain. Access to the CNS is also possible through the optic nerve.

BRIEF SUMMARY OF THE INVENTION

The efficient delivery of a pharmaceuticals to the mammal's nerve system (e.g. CNS) can be achieved by a device and method using iontophoresis through the olfactory nerve and the optical nerve in nasal cavity. The pharmaceuticals delivered can be any suitable substance that has an effect on the physiology of the recipient, including, but not limited to, traditional pharmaceuticals and nutritional supplements as well as nucleic acids and other macromolecules. Using this device and methodology, drugs are delivered to the CNS via a non-invasive transnasal or transocular nerve pathways. As a result, the pharmaceuticals can be delivered into the CNS, bypassing the blood-brain barrier, entering in all parts of the CNS and CSF.

Other objects, features and advantages of the invention will be apparent from the following detailed description of preferred embodiment thereof taken in conjunction with the accompanying drawing in which:

BRIEF DESCRIPTION OF THE DRAWINGS

FIG. 2.—Plasma levels of methylprednisolone hemisuccinate (MPS) and methyl prednisolone of rabbit no. 1 (0 mA, 1h.);

FIG. 3.—Plasma levels of methylprednisolone hemisuccinate (MPS) and methyl prednisolone of rabbit no. 2 (+3 mA, 1h.);

FIG. 4.—Plasma levels of methylprednisolone hemisuccinate (MPS) and methyl prednisolone of rabbit no. 3 (−3 mA, 1h.);

FIG. 5.—Plasma levels of methylprednisolone (MP) in rabbit no. 7 (−3 mA, 1h.);

FIG. 6.—Plasma levels of methylprednisolone hemisuccinate (MPS) and methyl prednisolone (MP) after 5 mg/kg i.v.does of MPS in rabbit no. 4;

DETAILED DESCRIPTION OF THE INVENTION

Figure 1A:
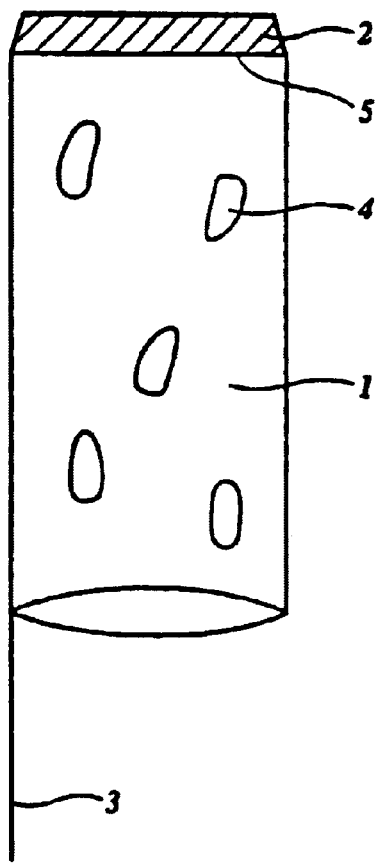
FIG. 1a is a cylindrical or tube shaped embodiment of an electrode according to the invention.

By using the olfactory nerve and the optic nerve we are thus able to deliver compounds into the CNS, bypassing the BBB; the compounds enter thus in all parts of the CNS and of course in the CSF.

The above methods relate to the non-invasive delivery of biologically active compounds into the brain (CNS).

Iontophoresis can enhance the delivery of drugs into the organism. The present invention relates in a first embodiment to a device to enhance the delivery of an effective amount of a biologically active compound into a target organ or tissue (nervous system) in a living organism, comprising at least two electrodes of which at least one can function as an active electrode and one as a passive electrode, said electrodes being capable of being positioned spaced apart from one another, at pre-selected locations of said organism, wherein the electrodes are all connected with a selected energy source, which generates and maintains an energy field before and during the enhancement of delivery of said compound under the influence of which said compound is propelled in a direction from the active to the passive electrode and into said target organ or tissue (nervous system). Due to the fact that an energy field is generated over an area which includes at least a part of the target organ or tissue (nervous system), it now appeared to be possible to deliver the active compound in a direction from the active to the passive electrode.

Preferably, the present device comprises an energy source which is provided with means for internal electrical circuiting, to hold the supply of energy in rest position, which means that it can activate the electrodes in the compound delivery position upon connection to said organism. Any type of electrical current including but not limited to DC and AC of any wave form, can be used for all variants which will be described in this application.

It is observed that said pre-selected locations are preferably with respect to the active electrode provided with the active substance: the nostril, or the bridge on the nose for the electrode without substance, with the substance applied in the nostril separately: and a supplementary pair of active and passive electrodes applied superficially.

It is found that the electrode acting as the active electrode is provided with means for carrying the active compound in a container of some sort. Such an arrangement has the advantage that the amount of active compound to be delivered to a target organ or tissue (nervous system) from a pre-selected place at some distance of said organ or tissue (nervous system) can be supplied as accurate as possible. If, for example, said active electrode, provided with the active substance of choice is placed in the nostril of an animal, or human being, and the passive electrode fixed on the back of the head, a generated electric field having a current intensity of up to 10 mA, will result in the almost complete penetration of the active substance into the brain.

In the present invention, the passive electrode may be split into two or more parts. It will then be possible to enhance the delivery of active substance more accurately to the desired organ or tissue (nervous system), for example by said split electrode, fixed at different places of the organism, sequentially. It is in this respect observed that at least one passive electrode must preferably be fixed at the projection at the skin of said living organism, of the target organ or tissue (nervous system) to which the biologically active compound will be delivered.

Furthermore, it is observed that a device for the delivery of a pharmaceutical agent or drug by means of iontophoresis, is already known from U.S. Pat. No. 5,298,017. This known device is adapted for the transmucosal and transdermal drug delivery and to prevent short-circuiting. Nevertheless, this known device is comprised of a plurality of essentially parallel elements, including the counter electrode and the donor electrode, which are indicated in the present invention as the passive and the active electrode respectively. The problem of this known device is still that burning effects might arise, because the intensity of the current used for generating the penetration of the drug must be rather high. The device according to the invention does not give rise to such short-circuiting problems.

It is further observed that if the electrodes are not connected with the power source, preferably an electric power source, the active compound will be diffused and dispersed randomly into said organism from the location onto which said compound was applied. Only by connecting both active and passive electrodes into the circuit, the active compound will be delivered directly into the target organ or tissue (nervous system).

With respect to the electrodes which can be used in the present invention, they are comprised of electrically conductive material such as a metal like aluminum, stainless steel, gold, silver, titanium, and zinc. Examples of other suitable electrically conductive materials include carbon, graphite, and metal salts like silver chloride. Electrodes may be formed of metal foil, metal screen, metal deposited or painted on a suitable carrier backing by means of calendaring, film evaporation, or by mixing the electrically conductive material in a polymer binder matrix. Alternatively, electrodes may be formed of a polymer matrix containing a conductive filler such as a metal powder, powdered graphite, carbon fibers, or other known electrically conductive filler material. Polymer based electrodes may be manufactured by mixing the conductive filler in a polymer matrix, preferably a mixture of hydrophilic and hydrophobic polymers. The hydrophobic polymers provide structural integrity, while the hydrophilic polymers may enhance ion transport. For example, metal powder, carbon powdered, carbon fibers and mixtures thereof can be mixed in a hydrophobic polymer matrix.

The energy source connected with the electrodes of the present device is preferably a source providing an electric field, a magnetic field, high energy waves like laser beams or ultrasonic waves, etcetera, in a special embodiment. The energy source may be a combination of these sources.

In another embodiment the, energy source is a source of thermal energy. Such a source can, of course also be combined with a source as mentioned above. For example, a combination of a source of electric energy and a source of thermal energy has the advantage that a compound with a relatively high molecular weight can be delivered in the organism, because the supply of thermal energy will allow a better penetration into tissues due to dilatation effects.

In an expedient embodiment of a device according to the invention, the energy source is provided with means for changing the polarity of the electrodes connected to said energy source, in order to prevent an irritation or burning sensation in tissues at the site of electrodes. The mechanism of irritation is related to the intensity and duration of the unidirectional current of ions into tissues, as introduced by means of iontophoresis. Electrochemical burns may originate from hydrogen and hydroxide ions generated by the DC current, where H+ ions accumulate at the anode and OH− ions at the cathode, leading to pH changes at both sites. These changes cause tissue damage and eventually to electrochemical burns. This can be avoided by the periodical reversal of current polarity in order to neutralize these ions.

By temporarily changing the polarity of the electrodes, it will then become possible to overcome potential limitations in the delivery of the active compound into the target tissue (nervous system). For, the changing of the polarity of the electrodes will result into a movement of the active compound in the reverse direction with respect to the initial direction.

The drug or other biologically active substance or compound can be selected from the following listed, and that are given as examples and without limitation: amino acids, anabolics, analgesics and antagonists, anesthetics, anthelmintics, anti-adrenergic agents, anti-asthmatics, anti-atherosclerotics, antibacterials, anticholesterolics, anti-coagulants, antidepressants, antidotes, anti-emetics, anti-epileptic drugs, anti-fibrinolytics, anti-inflammatory agents, antihypertensives, antimetabolites, antimigraine agents, antimycotics, antinauseants, antineoplastics, anti-obesity agents, anti-Parkinson agents, antiprotozoals, antipsychotics, antirheumatics, antiseptics, antivertigo agents, antivirals, appetite stimulants, bacterial vaccines, bioflavonoids, calcium channel blockers, capillary stabilizing agents, coagulants, corticosteroids, detoxifying agents for cytostatic treatment, diagnostic agents (like contrast media and radioisotopes), drugs for treatment of chronic alcoholism, electrolytes, enzymes, enzyme inhibitors, ferments, ferment inhibitors, gangliosides and ganglioside derivatives, hemostatics, hormones, hormone antagonists, hypnotics, immunomodulators, immunostimulants, immuno-suppressants, minerals, muscle relaxants, neuromodulators, neurotransmitters and neurotropics, osmotic diuretics, parasympatholytics, parasympathomimetics, peptides, proteins, psychostimulants, respiratory stimulants, sedatives, serum lipid reducing agents, smooth muscle relaxants, sympatholytics, sympathomimetics, vasodilators, vasoprotectives, vectors for gene therapy, viral vaccines, viruses, vitamins, oligonucleotides and derivatives, and any therapeutic agent capable of affecting the nervous system.

The invention further relates to electrodes to be used in a device according to the invention, comprising an electric conductive base member which can be connected to said selected energy source, wherein the top area of said base member is capable of supporting the biologically active compound, and all but the top area of said base member is coated with an insulating material.

The electrode should be inserted as deep as possible into the nose because of two reasons. As was mentioned before, in the upper part of the nasal cavity the BBB does not exist and can be bypassed, and secondly, the lower parts of the nasal cavity contain many capillaries and veins that provide easy access for the drugs to the bloodstream.

Preferably, the base member of the present electrode has a substantial frusto-conical hollow shape. Such a shape allows the easy insertion into a nostril; nevertheless, any other shape might do as well, such as a tube-like shape.

In an expedient embodiment, such an electrode according to the invention contains at least one hole or opening in the area coated with the insulating material present in the base member. Such an opening will prevent a complete blocking of the organ flow in which said electrode has been inserted, for example a nostril. In this way, it will be possible to continue normal breathing through the nose during the procedure.

According to an expedient embodiment, the electrode according to the invention is provided with a container for the active compound to be delivered, having a security-stop connection with the top area of the electrode. In this way it is possible to deliver a biologically active compound to a certain tissue or organ (nervous system) discontinuously without the necessity of removal and re-insertion of the present device.

The container can be made of any suitable material or combination of materials, that fulfills relevant criteria with respect relevant criteria with respect to compatibility with the drug or other substance or compound of interest and with the biological environment, but also with respect to ease of manufacturing, sterilizability, re-usability, low environmental impact, flexibility, connectibility, disposability and durability. Furthermore, the drug container or reservoir should be constructed of any material in such way that it is adapted to absorb and hold a sufficient quantity of liquid in order to permit transport of drug through its wall by means of iontophoresis, optionally, the container should hold a self-sealing membrane or valve that allows the in-situ refilling with drug solution, without the necessity of removal and re-insertion of the present device.

For example sponges, gauzes or pads consisting of cotton or other absorbent fabric, either or natural or synthetic origin, may be used. More preferably, containers or reservoirs are composed, at least in part, of one or more hydrophilic polymers. Typical preference is for hydrophilic polymers because water is the preferred ion transport medium and hydrophilic polymers have a relatively high equilibrium water content. Multilayered solid polymer container matrices are composed, at least in part of hydrophilic polymer. Insoluble hydrophilic polymer matrices are preferred over soluble hydrophilic polymers since the probability of delivering insoluble polymer by iontophoresis is very low.

The container matrix can be cross-linked with the drug components in place such as a silastic matrix, or the polymers can be prefabricated and sorbed with the components from solutions, for example with sponges or pads made of cellulose or woven fiber. The container may also consist of a gel matrix structure, or be of a classical reservoir type holding a liquid.

The polymers can be either of linear or cross-linked type.
Examples of suitable hydrophilic polymers include polyethylene glycols, polyacrylates, polyoxyethylene alkylethers, polyvidone, poloxamers, polyethylene oxides, polyvinyl alcohols, polyacrylamide, hydroxyethylcellulose, hydroxypropylcellulose, hydroxypropylmethyl-cellulase, co-polyesters, cyclodextrins, crospovidone, crosslinked dextrans, crosscarmellose sodium, natural gums, and starch, and mixtures thereof. optionally, the container matrix may contain a hydrophobic polymer, to improve structural integrity. Preferably the hydrophobic polymer is heat fusible in order to enhance the lamination of container layers.

Examples of suitable hydrophobic polymers include but are not limited to polyethylene, polypropylene, ethylene-vinylacetate copolymers, polyvinylacetate, polyisobutylenes, polyamides, polyurethanes, polyvinylchloride, and acrylic or methacrylic resins.

The container may be a polymeric matrix structure formed by mixing the selected drug, solvent, electrolyte, or other components with an inert polymer by means of melt blending, solvent casting, compression or extrusion.

The form of the container may be such as to enable its combination and attachment or coupling with the active electrode. The form, size and shape of the active electrode and its drug container are determined by the physiological, anatomical environment related to its application site, for instance in the nostril.

The connection of the container onto the active electrode may be of permanent or semi-permanent type, or of cartridge type for easy exchange of containers. Use of suitable adhesives for permanent connection of container and active electrode is foreseen, while physical locking and connecting means like slide lock, luer-lock, screw lock are more suitable for semi-permanent connections to enable exchange or cartridge type containers.

The energy source providing an electric field is preferably adapted to provide a current of up to 10 mA. Such a current appeared to be sufficient in practical tests. Nevertheless, it will be obvious for the expert that some deviation of this value might be used as well, and will also fall within the scope of the present invention.

The invention is also directed to an enhanced delivery of an effective amount of a drug into an internal target organ or tissue (nervous system) of an organism, such as a mammal, particularly a human being, being in need of such a delivery with such a drug, wherein the delivery of said compound is enhanced as such into said organ or tissue (nervous system) from a carrying location of said organism by means of energy-stimulated penetration generated and maintained by a field between at least two electrodes that may be split, upon connection with a selected energy source, of which electrodes one can function as an active electrode and one as passive electrode, of which at least one electrode is placed on the outer layer of said organism, and one electrode, having the opposite polarity, is placed near the place where said active compound is applied.

It is in this respect observed that the passive electrode must be fixed at a place on the skin of the organism, which is the projection of the target tissue (nervous system) to be treated with the biologically active compound, for example when the active compound is administered directly to the CNS via the nose, the active electrode is placed in the nose, while the passive electrode is placed on the back of the head. To obtain the desired effects, the passive electrode is wetted with a water solution or hydrogel or an electricity conducting adhesive before its fixation to the skin, whereas the active electrode is provided with the active compound before its fixation. It is nevertheless also possible to use a hydrogel or conductive adhesive onto the container of the active compound, for example in order to temporarily allow fixation onto the outside of a tumor.

For example a patient with a tumor in the right temporal lobe. In this case the active electrode with the drug is inserted in the nasal cavity and of the split passive electrode one part is fixed on the back of the head and the other part is fixed on the right temporal region an the projection of the tumor. Then the drug is delivered into the brain and the concentration will be much higher in the region of the tumor. Preferably the location of the active electrode holding the drug container is spaced apart from the target tissue by a membrane or tissue having low resistance. A direct penetration, for example from the nasal cavity into the brain, is thus possible due to the absence of the blood-brain barrier.

According to the invention, it now also appeared to be possible to enhance the delivery of the biologically active compound from its carrying location to said target organ or tissue (nervous system), without any substantial distribution into surrounding parts of the organism, for example the bloodstream.

According to a preferred embodiment, the delivery of said active compound is enhanced transnasally to the CNS from the nostril bypassing the BBB by using a current intensity of up to 10 mA between an active electrode introduced into at least one nostril, and a passive electrode fixed on the back of the head or another place of the head.

According to a variant of this embodiment the delivery of said compound is enhanced transnasally to the CNS by using an active electrode fixed externally on the nose of the organism, a passive electrode fixed an the back of the head or another place, while the active compound is applied intranasally after the generation of the energy field.

Expediently, the active electrode is split into two parts, one of which is fixed externally to the nose, and the other one, being provided with the said active compound is introduced into a nostril.

According to a further variant of the invention, the delivery of said compound is enhanced into some specific region of the brains by using an active electrode fixed intranasally or extranasally and a split passive electrode, whereof one part is fixed externally on the projection of said specific region on the head, and another part is fixed on the back of the head or another place of the head, while said compound has been applied into a nostril.

For the delivery of the active compound in a certain hemisphere or part of a hemisphere it is necessary to fix the active electrode into one nostril and to fix the split passive electrode on the mastoideus, or another place of the body, and on the projection of the tumor.

It is observed that an embodiment comprises a kit consisting of two different sets of active and passive electrodes, wherein one set consisting of an active electrode to be placed into a nostril and being provided with a biologically active substance, and a passive electrode to be fixed on the back of the head; and another set consisting of an electrode, wetted in a water solution, to be fixed at the part of the head opposite to the place of treatment, and another electrode wetted in a water solution to be fixed on the projection of the place of treatment, wherein both sets of electrodes can be connected to two different sources, if desired, or to one source, will also fall within the claimed scope of protection of the present invention.

It is further observed that the present type of iontophoresis (i.e. according to the invention) can be combined with other methods which are suited for the delivery of biologically active compounds. Examples for such methods are diathermy, use of magnetic field, use of ultrasonic energy, high energy like laser etc., or use of compounds providing a dilatation effect. These dilatating compounds can either be administered separately via oral or parenteral routes or be combined with the drug delivered via iontophoresis. Diathermy and dilators are preferred when the delivery of biologically active compounds having a high molecular weight must be enhanced through some tissue of the body, for example bypassing the BBB.

According to a variant embodiment of the process according to the invention, the compound is enhanced transocular to the CNS from the eyelid by using a current intensity of up to 10 mA between an active electrode fixed over the active compound carried by said eyelid, and a passive electrode fixed on the back of the head or on the mastoids of the organism.

The Present Invention is Further Explained in the Following Practical Embodiments.

a) We suggest realization of iontophoresis according to a first embodiment, through the nasal cavity. We called this method intracerebral transnasalis. Our method has the following advantage. The mucous membrane of the nasal cavity has a low electrical resistance. Therefore, according to ohms law the current intensity by the same voltage is much higher than during transdermal iontophoresis. It is known that the quantity of substance introduced by current is directly proportional to the current intensity. Hereby, the proportion of the substance introduced into an organism (into the brain) will be higher than if it were done through the skin. The concentration of the substance in the blood introduced by our method will be low or absent. Thus side effects caused by entrance of the substance into the systemic circulation will be minimal, in contrast to intravenous and oral administration.

We Suggest the Following Method for This Embodiment.

Two electrodes (metal, conductive rubber or another conductive material, such as mentioned before) must be introduced into the nostrils. The electrodes have to be covered by the cotton or other material wetted in the solution of the necessary drug or compound and to touch the nose mucous membrane. Electrodes must be introduced as deep as possible, but without causing unpleasant feelings. Electrodes themselves must touch neither skin nor the nose mucous membrane, only through the container with active substance.

Another electrode or split electrode covered by cotton or other material and wetted in a water solution has to be fixed on the mastoid processes or to be fixed on the back of the head in the area of cervical vertebrae or another place. Depending on individual tolerance (pressure or some other unpleasant feelings), current intensity can increase up to 10 mA. Subsequently the current intensity can be decreased until any unpleasant feeling disappears.

b) We suggest realization of iontophoresis according to a second embodiment through the eyeballs. We called this method intracerebral transocularis. Our method has the following advantage. The skin of the eyelid has a resistance lower than that on the rest of the skin surface and a resistance of the cornea and of the sclera is negligible.

We Suggest the Following Method for This Embodiment.

A split active electrode (metal, conductive rubber, or another conductive material) must be placed over the eyes. The active electrodes have to be covered by the cotton or other material wetted in the solution of the necessary active substance and to touch the skin. Electrodes themselves must not touch the skin, but only through the container (here the cotton) holding the active substance. Another split electrode covered by cotton or other material and wetted in a water solution has to be fixed on the mastoid processors or on another place or a single passive electrode has to be fixed on the back of the head in the area of cervical vertebrae or on another place. Depending on individual tolerance (pressure or some other unpleasant feelings), current intensity can increase up to 10 mA. Subsequently the current intensity can be decreased until unpleasant feelings disappear. This method is called transocular.

Variations of this method called transcorneal and transscleral are realized by applying two special electrodes directly to the cornea and the sclera, respectively. The electrodes brought in the contact with the cornea or the sclera must deliver the necessary drug or active substance. Another split electrode covered by cotton or other material and wetted in a water solution has to be fixed on the mastoid processes or one part of the passive electrode has to be fixed on the back of the head in the area of cervical vertebrae on another place, and another part has to be fixed on the forehead. Depending on individual tolerance (pressure or some other unpleasant feelings), current intensity can increase up to 2 mA or more.

It is observed that the above mentioned embodiments must not be interpreted as being limitative. Other embodiments which are obvious for the expert upon reading the description and claims will fall within the scope of the present invention.

Figure 8A:
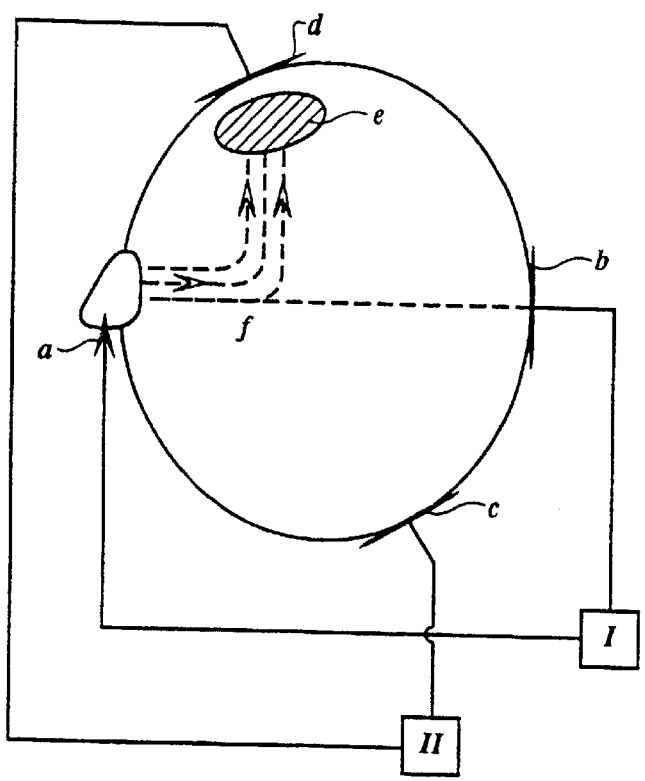
FIGS. 8a & 8b—showing the conveyance route of an active substance from a nostril into the brain.
Figure 8B:
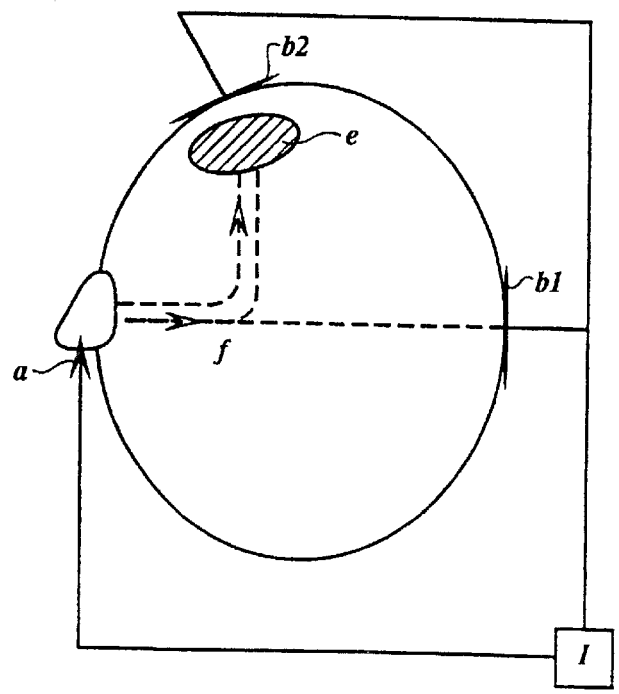
Figure 2:
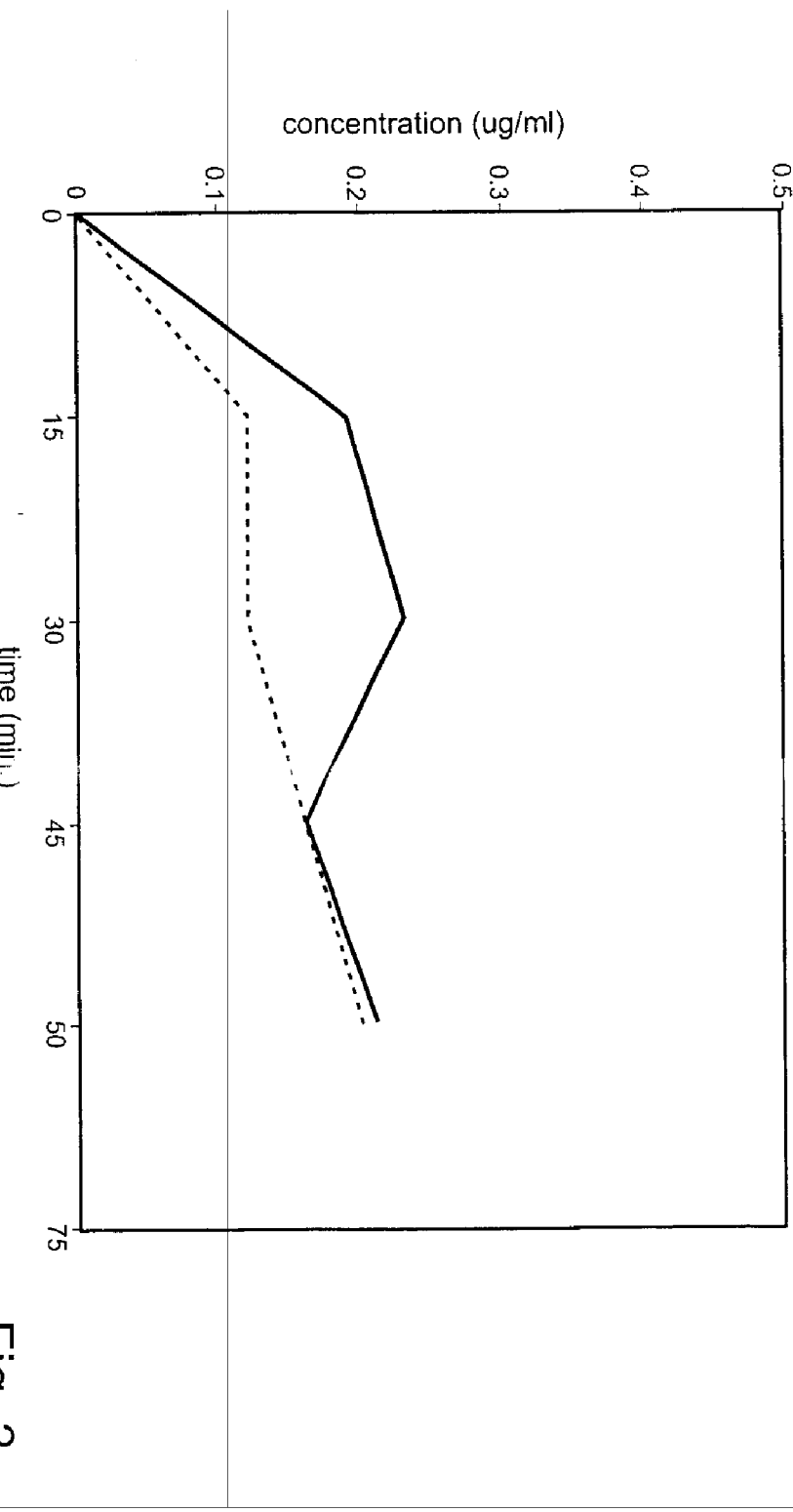
Figure 3:
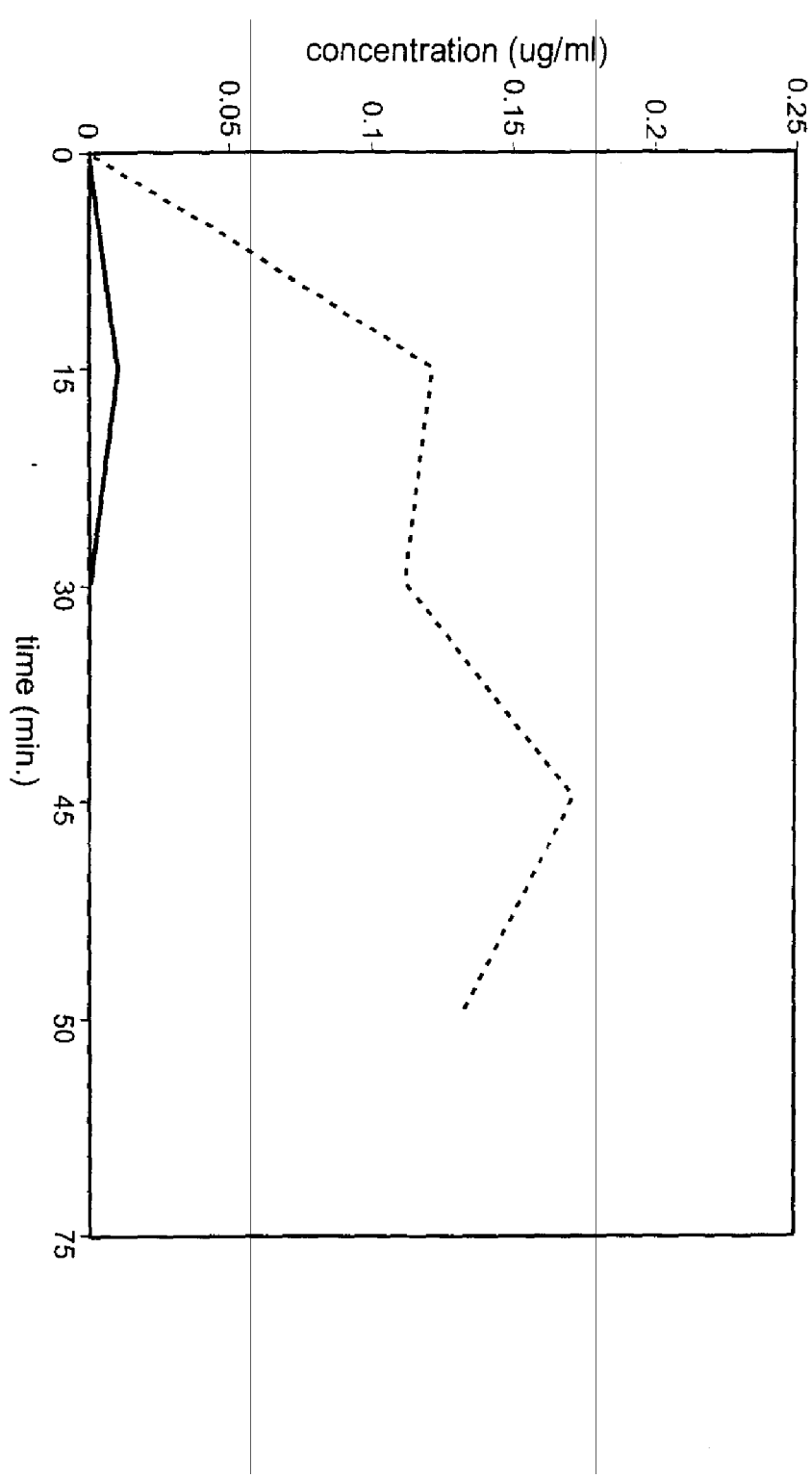
Figure 4:
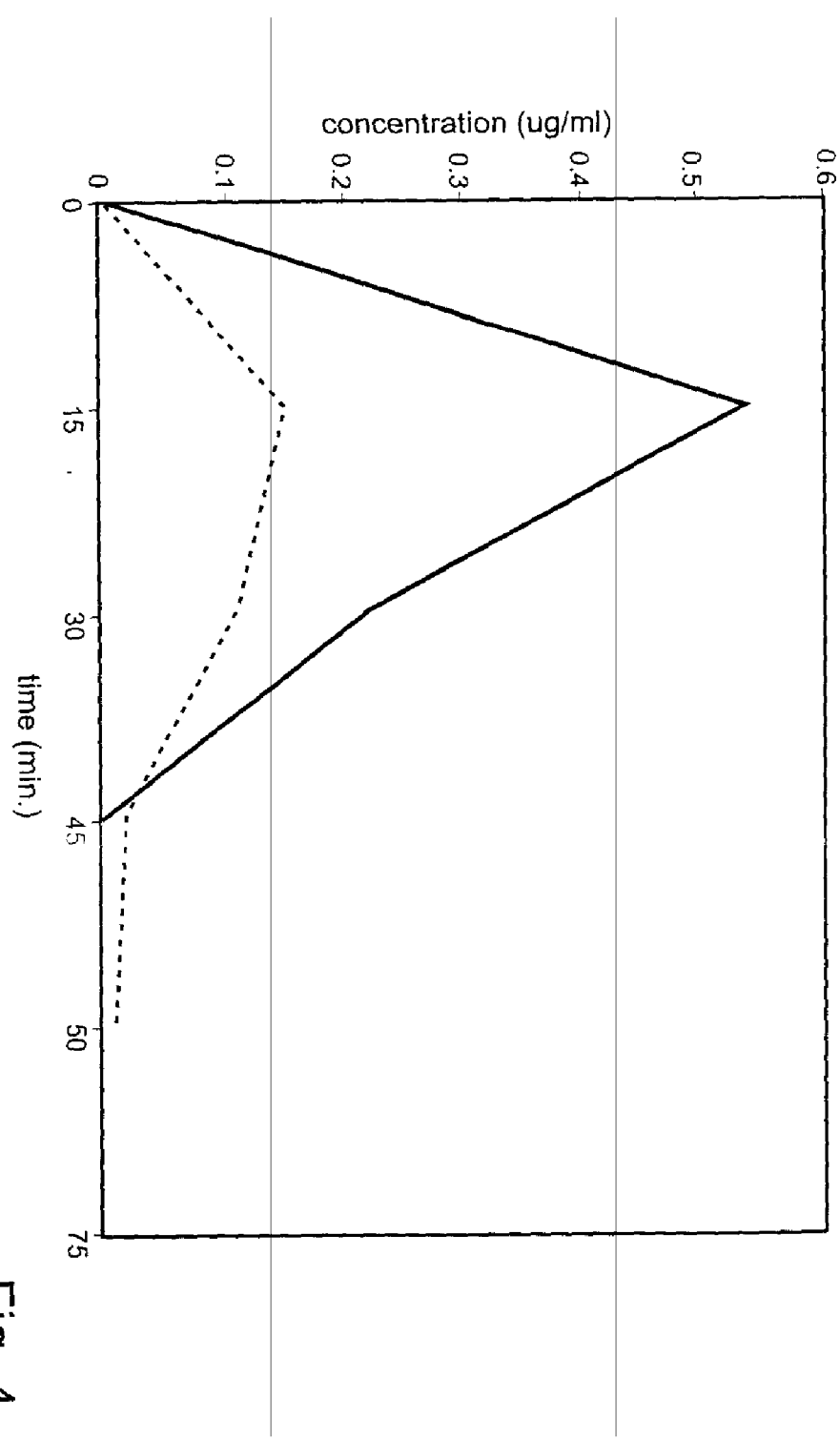
Figure 5:
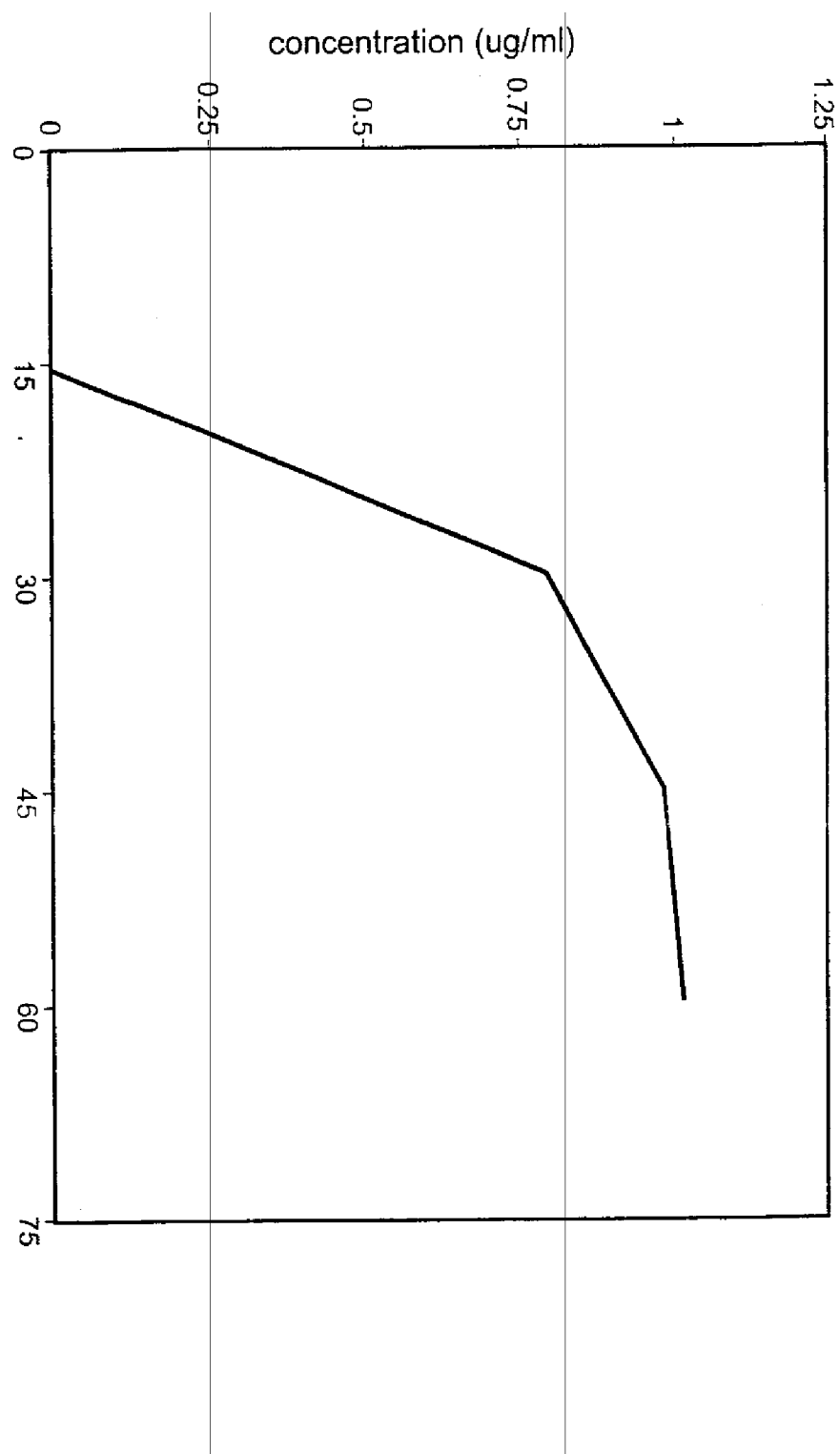
Figure 6:
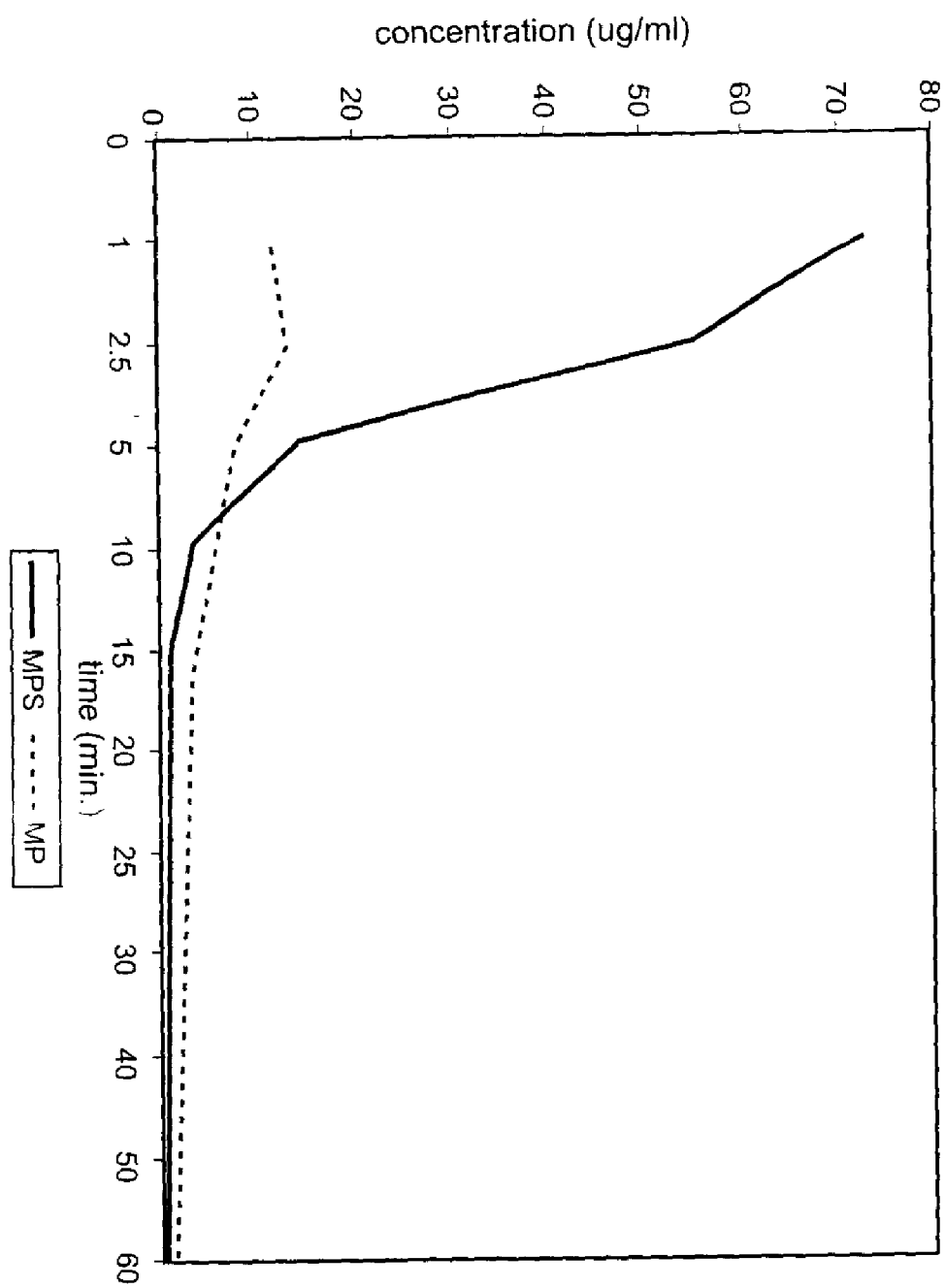

The invention will be explained further in the following examples and the accompanying drawings wherein FIG. 1—shows a particular embodiment of an electrode according to the invention, whereas FIGS. 2 to 7 show graphically the results obtained by using a device and method according to the invention, while FIGS. 8a and 8b show the conveyance route of an active substance from a nostril into the brain.

Figure 1B:
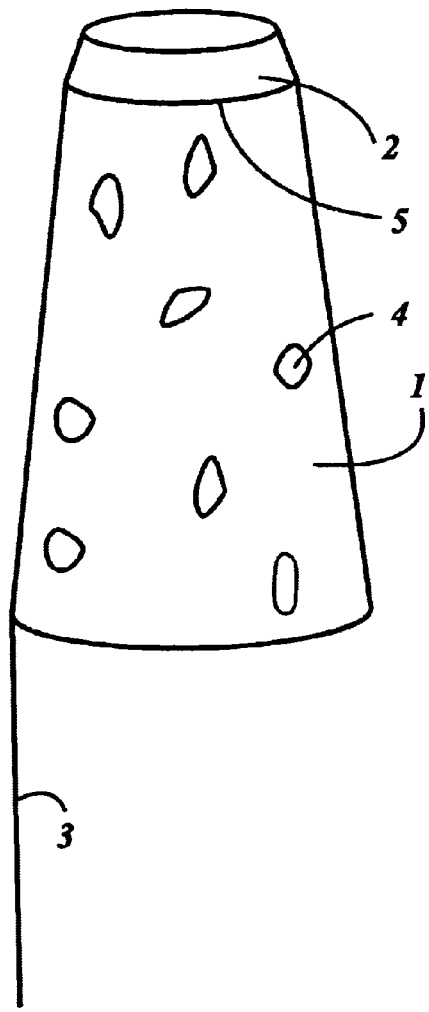
FIG. 1b is a frusto-conical-shaped embodiment of an electrode according to the invention.

In FIG. 1, the electrode comprising the conductive base member is represented by 1; this base member has preferably a hollow form, and is expediently coated with an insulating material for example a plastic, except the top areas, which carries the biologically active substance 2. The base member 1 is further connected to a source of current by means of line 3, connected to the conductive base material. The base member is further provided with one or more perforations 4. Although the electrode as represented in the figure has a tube-like form, a substantial frusto-conical form or another form can be used. Further, the perforations 5 can have any form.

In FIGS. 8a and 8b the delivery of an active compound into the brain is schematically shown.

More specifically the compound is according to FIG. 8a applied into a nostril by means of the active electrode a. The passive electrode b is fixed on the back of the head.

Both electrodes are connected with an energy source I. Upon activation of the electrodes a and b the active compound will be forced in a direction from a to b, as indicated by dotted lines f. To enhance the delivery of active compound into the target tissue e, for example to a tumor, the direction of delivery of the active substance can be bend by means of another pair of electrodes, i.e. one electrode c and another electrode d. These electrodes c and d are connected to a different energy source II.

It is nevertheless possible, according to a special embodiment, as shown in FIG. 8b, to use a split passive electrode, consisting of passive electrode b1 and passive electrode b2, both being connected with energy source 1. Also in this case, the direction of delivery of the active substance from the nostril into the brain has been given by dotted lines f.

EXAMPLE 1

We conducted the transnasal iontophoresis in 60 patients and in 20 healthy volunteers in the age from 20 to 40. Forty-five of 60 patients suffered from vegetative distonia with sleep disorders, 40 of which showed significant improvement, 4 have showed no improvement, and the rest have showed some improvement. These patients were administered the antidepressant amitryptiline. The other 15 of 60 patients suffered from migraine headaches. These patients were administered Papaverine hydrochloride. Twelve of them have showed significant improvement and 3 showed no improvement.

Iontophoresis sessions were conducted daily for 15–30 minutes, with a total of 20–25 sessions. As a rule, the improvement came after 3–5 sessions. To healthy volunteers we administered a solution of piracetam. 16 of them have shown significant improvement of memorizing abilities and increase of activity.

Another experiment was conducted in 5 male volunteers in the age from 20 to 30. We investigated penetrability of benzylpenicillin introduced transnasally into the cerebrospinal fluid (CSF) and into the blood. At he beginning we carried out an endolumbal puncture with each subject, taking 1 ml of the CSF. The needle was left in place of the puncture for the duration of the experiment (1.5–2 hours). Then we took 1 ml of blood from the arm vein. Both fluids were subsequently investigated for the presence of benzylpenicillin by means of a microbiological assay. This analysis was conducted as follows. We took three Petri dishes with the Streptococcus culture. The first dish remained only with the streptococcus culture. To the second one was added one drop of the CSF. To the third one was added one drop of blood from the vein. All three dishes were subsequently placed into a thermostat to analyze the ability of the CSF and the blood to destroy the streptococcus. Then we wetted cotton covers in the benzylpenicillin solution (0.2 g [200 000 units] per 5 ml of distilled water). A split electrode covered by these cotton covers was introduced deeply into both nostrils. Another split electrode covered by cotton wetted in water was fixed on the mastoid processes. The intensity of galvanic current by the iontophoresis was 2.0 mA.

The duration of the procedure was 30 minutes. In 1.5 hour after the iontophoresis with benzylpenicillin again 1 ml of the CSF and 1 ml of the blood were taken. Following the same procedure described above we investigated them for the presence of benzylpenicillin, we found out that after 1.5 hour of iontophoresis, the CSF showed significant presence of benzylpenicillin. However, no benzylpenicillin could be demonstrated in the blood since no lysis of the streptococcus occurred. This was a direct evidence that the iontophoresis allowed benzylpenicillin to penetrate into the brain tissue without entering the blood.

EXAMPLE 2

An experiment with the transocular method was conducted in 5 male volunteers in the age from 20 to 30. We investigated the penetration of benzylpenicillin introduced transocular into the cerebrospinal fluid (CSF) and into the blood. At he beginning we carried out an endolumbal puncture with each subject, taking 1 ml of the CSF. The needle was left in place of the puncture for the duration of the experiment (1.5–2 hours). Then we took 1 ml of blood from the arm vein. Both fluids were subsequently investigated for the presence of benzylpenicillin by means of a microbiological assay. This analysis was conducted as follows. We took three Petri dishes with the Streptococcus culture. The first dish remained only with the streptococcus culture. To the second one was added one drop of the CSF. To the third one was added one drop of blood from the vein. All three dishes were subsequently placed into a thermostat to analyze the ability of the CSF and the blood to destroy the streptococcus.

Then we wetted cotton covers in the benzylpenicillin solution (0.2 g [200 000 units] per 5 ml of distilled water). A split electrode covered by these cotton covers was placed over each of the eyes. Another split electrode covered by cotton wetted in water was fixed on the mastoid processes. The intensity of galvanic current by iontophoresis was 0.8–2 mA. The duration of the procedure was 30 minutes. In 1.5 hour after iontophoresis with benzylpenicillin we took again 1 ml of CSF and 1 ml of blood. Following the same procedure described above we investigated them for the presence of benzylpenicillin. We found that after 1.5 hour of iontophoresis, the CSF showed significant presence of benzylpenicillin. However, no benzylpenicillin could be demonstrated in the blood since no lysis of the streptococcus occurred. This was a direct evidence that the iontophoresis allowed the benzylpenicillin to penetrate into the brain tissue without entering the blood.

Electric current does not have a negative impact on the brain and is even used for treatment of a series of the nervous system disorders. This treatment is called cerebral electrostimulation or electrosleep. This method is realized by application of electrodes bilaterally placed over the eyes and the mastoid or neck region.

One of the most comprehensive overviews of transocular iontophoresis has been given by Sarraf and Lee.

EXAMPLE 3

Methylprednisolone hemisuccinate was according to the invention administered to rabbits, using the following protocols.

Materials and Methods

HPLC assay for methylprednisolone hemisuccinate and methylprednisolone: The mobile phase was a mixture of acetonitrile and 0.1 M phosphate buffer pH 6 (30:70% v/v). The flow rate was 1.2 ml/min. The effluent was monitored at 242 nm. Injection volume 20 µl. Retention times: methylprednisolone hemisuccinate (MPS) 6.5 min. and methylprednisolone (MP) 14.6 min. Limits of quantitation 10 ng/ml for both compounds. Intra and interday coefficients of variation were <5%. CASno. MPS 2375-03-3; MP 83-43-2. Molecular weight: MPS 496.50; MP 374.50. Gross formula: MPS $C_{26}H_{33}NaO_8$.

1000 mg Methylprednisolone hemisuccinate sodium (Solumedrol®, batch 12/2000A 95LI3 CL102, Upjohn, Ede, the Netherlands) was dissolved in 5 ml distilled water (200 mg/ml).

Animals

New Zealand White rabbits (2.5–3 kg body weight) were obtained from the Central Animal Laboratory (University of Nijmegen, the Netherlands). The animals were anaesthetized with 0.5 ml/kg Hypnorm (fentanylcitrate 0.315 mg/l and fluanisone 10 mg/ml; Janssen Pharmaceutica, Tilburg, the Netherlands). The animals were intubated and mechanically ventilated with N20, 02 1:2 (v/v), and ethrane 2.4%. Endtidal C02 was maintained at 4%. The artery femoralis was cannulated with a Venflon 2, 18 G catheter.

Mechanical ventilation was maintained with an Amsterdam Infant Ventilator MK2 (Hoek Loos, Amsterdam, the Netherlands) and a Capnomac (Datex, Hoevelaken, the Netherlands). At the end of the experiment the animals were killed by an arterial injection of 2 ml pentobarbital 60 mg/ml (Narcovet®, Apharmo, Arnhem, the Netherlands).

Iontophoresis

A stimulator was used. The applied current was 3 mA, at 8000 Hz, pulse duration 119 µs, puls interval 6 µs. Remark: this type of current was used because it is less irritating at the nerve ending and is therefore less painful. Electrodes, encapsulated in cotton wool and saturated with drug solution were firmly placed in the nasal passage, the opposite electrode was placed with a wet sponge pad at the shaven back of the head (clear skin). The nose electrodes were used in the positive (+) and negative (−) mode in separate experiments.

Sampling

Blood samples (2 ml) of each animal were collected in heparinized polypropylene tubes just before the start of iontophoresis (t=0) and at 15, 30, 45 and 60 min. after the start of the stimulation. A spinal fluid sample of 1 ml was collected from the animal after killing and just before the brain was dissected. The right Temporal lobe, the Frontal lobe, Brain stem and brain remainings were collected.

Sample Preparation

During the whole experiment (6 h.), blood samples were kept at room temperature (20° C.). Thereafter the blood samples were centrifuged at 3000 g for 5 min. and plasma was stored in duplo at −20° C. until analysis. Brain and liquor were stored at −20° C. until analysis.

Drug Analysis

The HPLC system consisted of a Marathon autosampler (Separations, Hendrik ido Ambacht, the Netherlands), a Spectra Systems P4000 quaternary gradient pump, a Spectra Systems UV 1000 detector (Thermoseparations, Breda, the Netherlands) and a Hitachi D2500 integrator (Merck, Amsterdam, the Netherlands). The column was a Spherisorb 5 ODS (250*4.6 mm) with a guard column (15*4.6 mm) packed with 5 µm C 18 reversed phase material (Chrompack, Bergen op Zoom, the Netherlands).

Sample Handling

150 µl plasma was vortexed for 10 s with 150 µl acetonitrile. The mixture was centrifuged at 3000 g for 5 min. 20 µl of the clear supernatant was injected onto the column. Brain tissue. 2 ml of distilled water was added to 1 gram of brain tissue. The mixture was homogenized with an ultratorax apparatus (Ystral, Dottingen, Germany) at 10.000 rpm during 30 seconds. The homogenate was centrifuged at 3000 g during 5 min. and further treated like plasma.

Rabbit 1

Two cotton wools, saturated with MPS 200 mg/ml were placed for one hour in the nostrils.

Rabbit 2

Two cotton wools and electrodes, saturated with MPS 200 mg/ml were placed for one hour in the nostrils. Stimulation with +3 mA.

Rabbit 3

Two cotton wools and electrodes, saturated with MPS 200 mg/ml were placed for one hour in the nostrils. Stimulation with −3 mA.

Rabbit 4

5 mg/kg (12.5 mg) MPS was given intravenously in 5 min. Blood samples were taken at 0, 1, 3, 5, 10, 15, 20, 25, 30, 40, 50 and 60 min. Brain samples were taken.

Rabbit 5

1 mg/kg (2.5 mg) MPS was given intravenously in 5 min. Blood samples were taken at 0, 1, 3, 5, 10, 15, 20, 25, 30, 40, 50 and 60 min. Brain samples were taken.

Rabbit 6

Two cotton wools and electrodes, saturated with MPS 200 mg/ml were placed for one hour in the nostrils. Stimulation with—1 mA.

Rabbit 7

Two cotton wools and electrodes, saturated with MPS 200 mg/ml (dose 100 mg; the electrodes were dipped in a 1 ml solution) were placed for one hour in the nostrils. Stimulation with—3 mA.

TABLE 1

Plasma concentrations (μg/ml) of methylprednisolone hemisuccinate (MPS) and methylprednisolone (MP) in a rabbit after installation of a MPS saturated cotton wool in the nostrils of each rabbit and without and with positive and negative iontophoresis.

| Time | rabbit no. 1 (0 mA, 1 h) | | rabbit no. 2 (+3 mA, 1 h) | | rabbit no. 3 −3 mA, 1 h | |
|---|---|---|---|---|---|---|
| (min.) | MPS | MP | MPS | MP | MPS | MP |
| 0 | 0 | 0 | 0 | 0 | 0 | 0 |
| 15 | 0.19 | 0.12 | 0.01 | 0.12 | 0.54 | 0.15 |
| 30 | 0.23 | 0.12 | 0 | 0.11 | 0.22 | 0.11 |
| 45 | 0.16 | 0.16 | 0 | 0.17 | 0 | 0.02 |
| 60 | 0.21 | 0.20 | 0 | 0.13 | 0 | 0.01 |

(+) means: positive electrode in the nostril;
(−) means: negative electrode in the nostril.

The concentrations of both substances in the brains were also measured. The following results were obtained for the concentrations of the compounds in the brains.

TABLE 2

Brain concentrations (μg/g) of methylprednisolone hemisuccinate (MPS) and methylprednisolone (MP) in a rabbit after installation of a MPS saturated cotton wool in the nostrils of each rabbit and without and with positive and negative iontophoresis.

| | Rabbit numbers | | | | | |
|---|---|---|---|---|---|---|
| | 1 (0 mA, 1 h) | | 2 (+3 mA, 1 h) | | 3 (−3 mA, 1 h) | |
| tissue | MPS | MP | MPS | MP | MPS | MP |
| frontal lobe | 0 | 0 | 0 | 0 | 0 | 1.20 |
| temporal lobe right | 0 | 0 | 0 | 0 | 0 | 0.52 |
| brain stem | 0 | 0 | 0 | 0 | 0 | 3.73 |
| brain remains | 0 | 0 | 0 | 0 | 0 | 0.70 |

Figure 2:
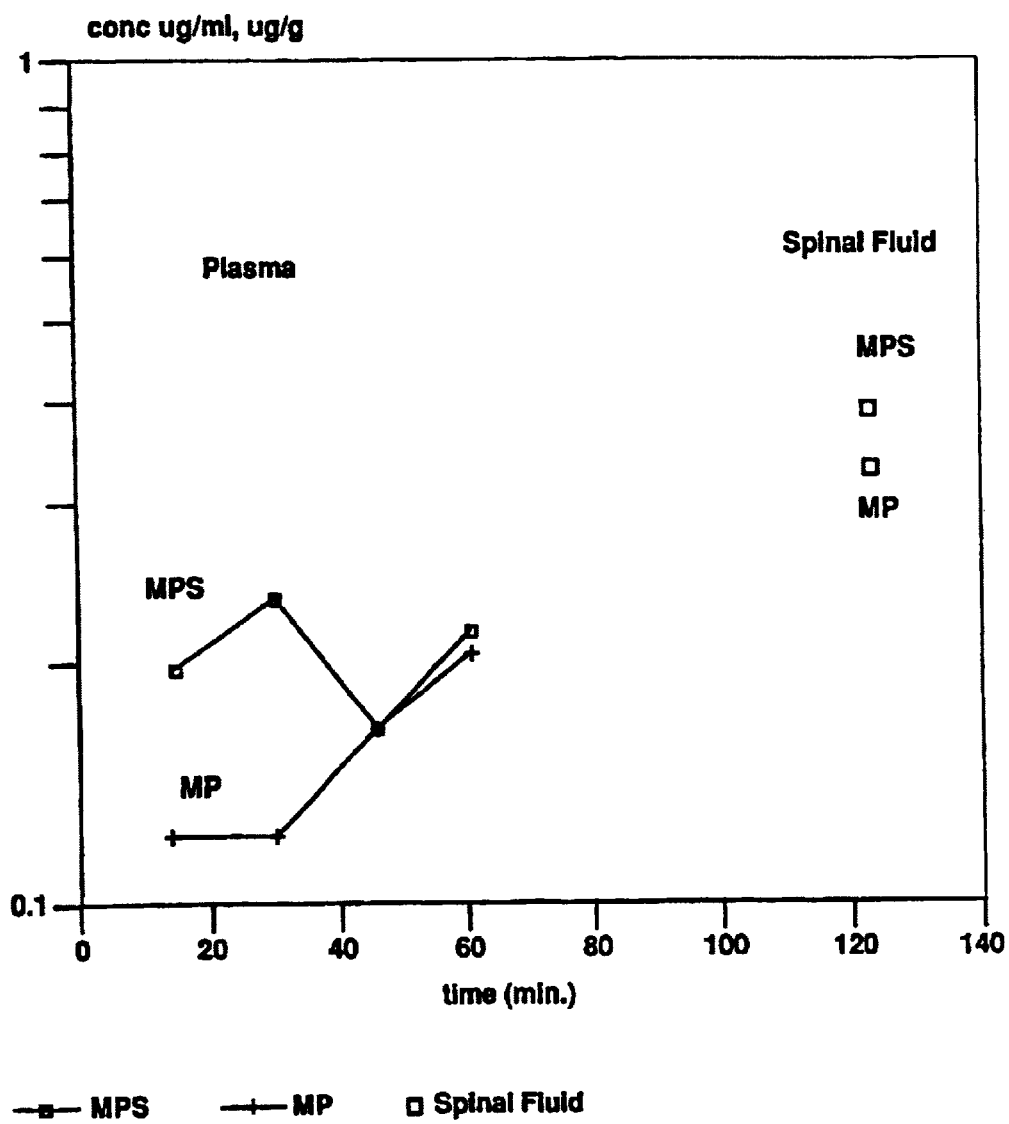
FIGS. 2 to 6 are concentrations vs. time graphs and FIG. 7 a bar graph all by, are showing graphically the results obtained by using a device and method according to certain embodiments of the invention, i.e.

FIG. 2 shows the results obtained with rabbit no. 1 graphically

Figure 3:
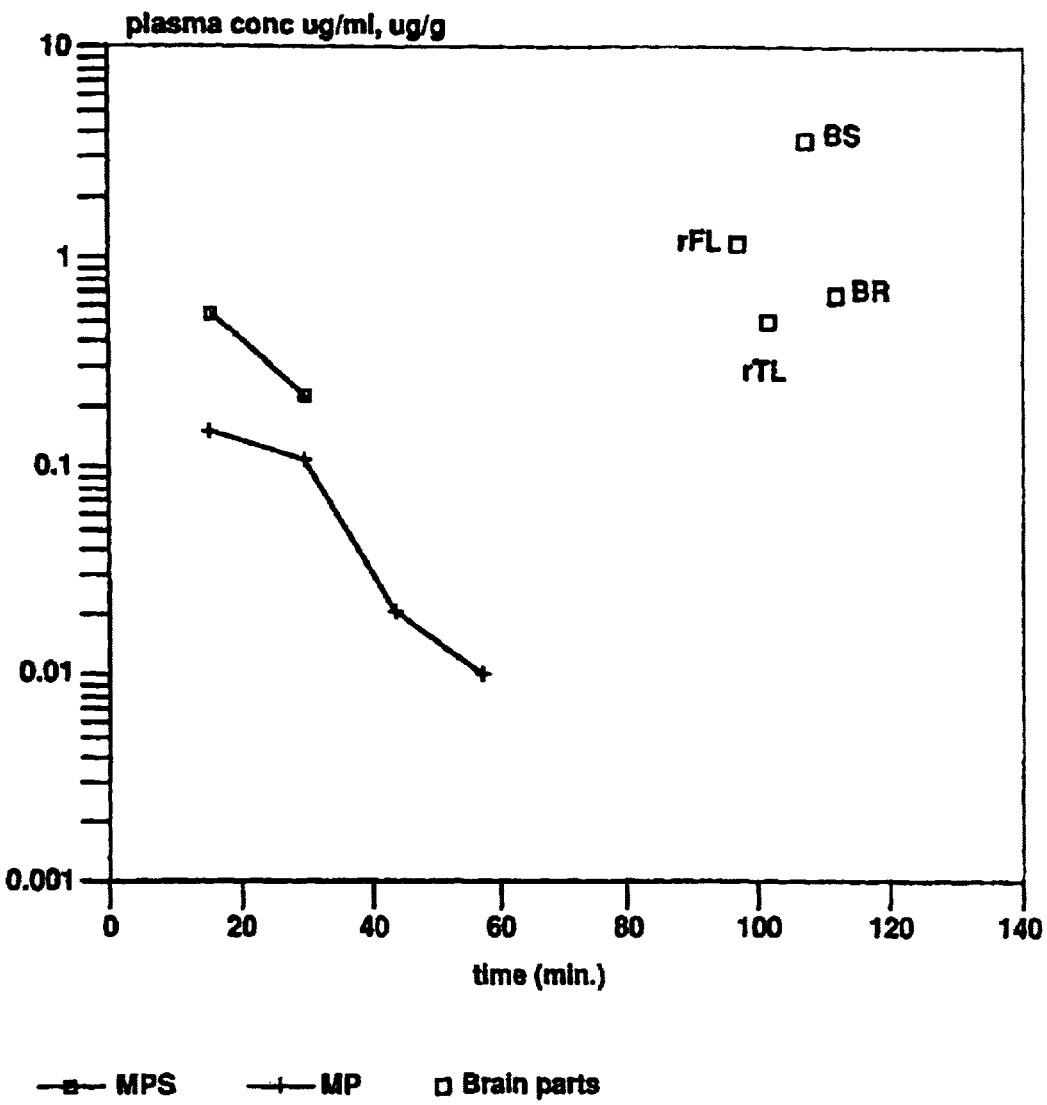

FIG. 3 shows the results obtained with rabbit no. 2 graphically

Figure 4:
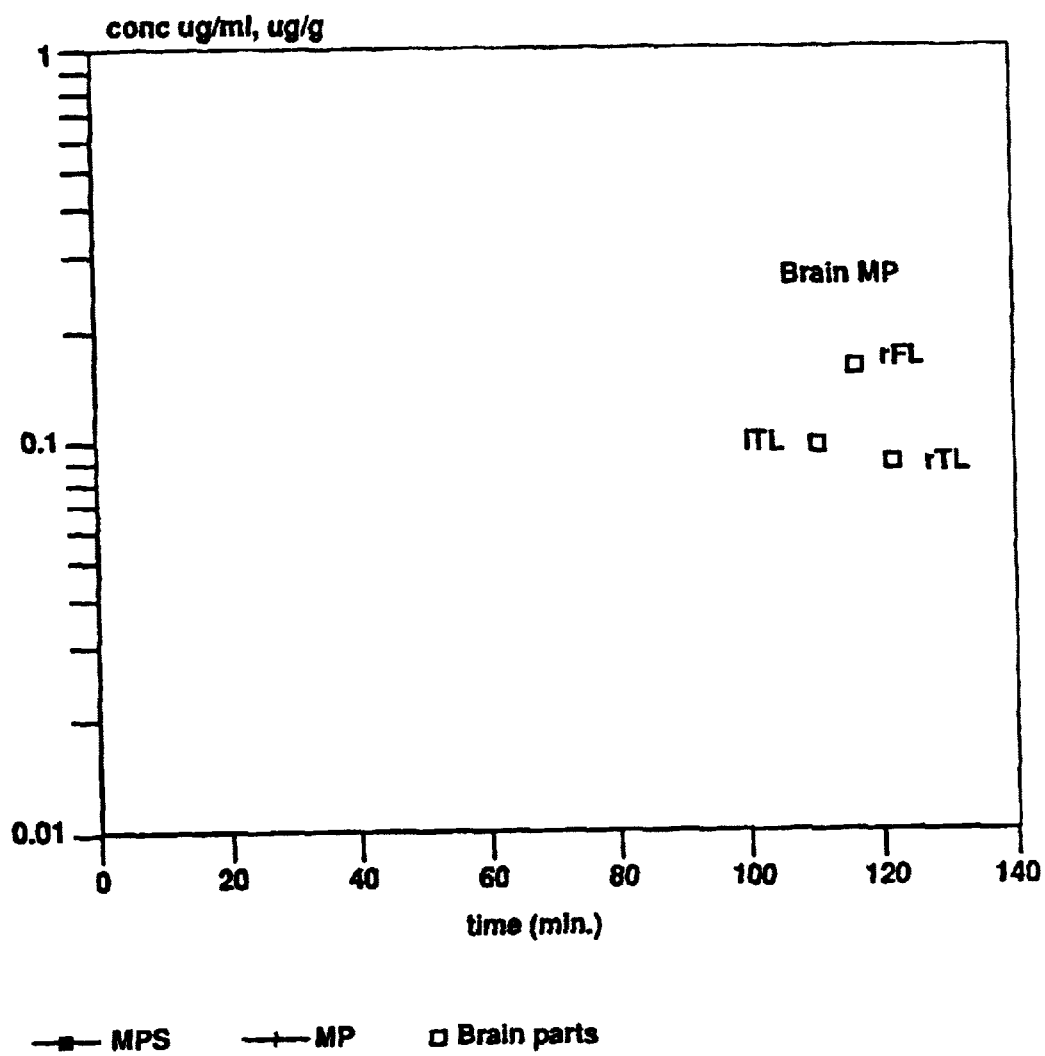

FIG. 4 shows the results obtained with rabbit no. 3 graphically

The values obtained with rabbit no. 2 (Table 2) compared with those obtained with rabbit no. 3 show that a positive electrode into the nostril is the wrong polarity, whereas the negative electrode is the right polarity for this kind of substance.

TABLE 3

Plasma concentrations (μg/ml) of methylprednisolone hemisuccinate (MPS) and methylprednisolone (MP) in a rabbit after installation of a MPS saturated cotton wool in the nostrils and negative iontophoresis.

| Time | rabbit no. 6 (−1 mA, 1 h) | |
|---|---|---|
| (min.) | MPS | MP |
| 0 | 0 | 0 |
| 15 | 0 | 0 |
| 30 | 0 | 0 |
| 45 | 0 | 0 |
| 60 | 0 | 0 |
| spinal fluid | 0 | 0 |

TABLE 4

Brain concentrations (μg/g) of methylprednisolone hemisuccinate (MPS) and methylprednisolone (MP) in a rabbit after installation of a MPS saturated cotton wool in the nostrils and negative iontophoresis.

| | rabbit no. 6 (−1 mA, 1 h) | |
|---|---|---|
| Tissue | MPS | MP |
| right frontal lobe | 0 | 0 |
| left frontal lobe | 0 | 0.16 |
| right temporal lobe | 0 | 0.09 |
| left temporal lobe | 0 | 0 |
| cerebellum | 0 | 0 |
| brain stem | 0 | 0 |
| brain rest | 0 | 0 |
| cervicalis spinal cord | 0 | 0 |
| thoracilis spinal cord | 0 | 0 |
| lumbalis spinal cord | 0 | 0 |

From the results of the tables 3 and 4 it appears that a current intensity of 1 mA is probably too small to effect an acceptable transport of the drug to all parts of the brain. Results are graphically given in FIG. 7

TABLE 5

Plasma concentration (μg/ml) of methylprednisolone hemisuccinate (MPS) and methylprednisolone (MP) in a rabbit after installation of a MPS saturated cotton wool in the nostrils and negative iontophoresis.

| Time | rabbit no. 7 (− | |
|---|---|---|
| 0 | 0 | 0 |
| 15 | 0 | 0 |
| 30 | 0.98 | 0.78 |
| 45 | 0.40 | 0.97 |
| 60 | 0.25 | 1.00 |
| spinal | 0.30 | 1.16 |

TABLE 6

Brain concentrations (μg/g) of methylprednisolone hemisuccinate (MPS) and methylprednisolone (MP) in a rabbit after installation of a MPS saturated cotton wool in the nostrils and negative iontophoresis.

| | rabbit no. 7 (−3 mA, 1 h) | |
|---|---|---|
| Tissue | MPS | MP |
| right frontal lobe | 0 | 0.95 |
| left frontal lobe | 0 | 1.84 |
| right temporal lobe | 0 | 2.27 |
| left temporal lobe | 0 | 0.36 |
| cerebellum | 0 | 0.69 |
| brain stem | 0 | 0.41 |
| brain rest | 0 | 1.71 |
| cervicalis spinal cord | – | – |
| thoracilis spinal cord | 0 | 0.10 |
| lumbalis spinal cord | – | – |

Figure 5:
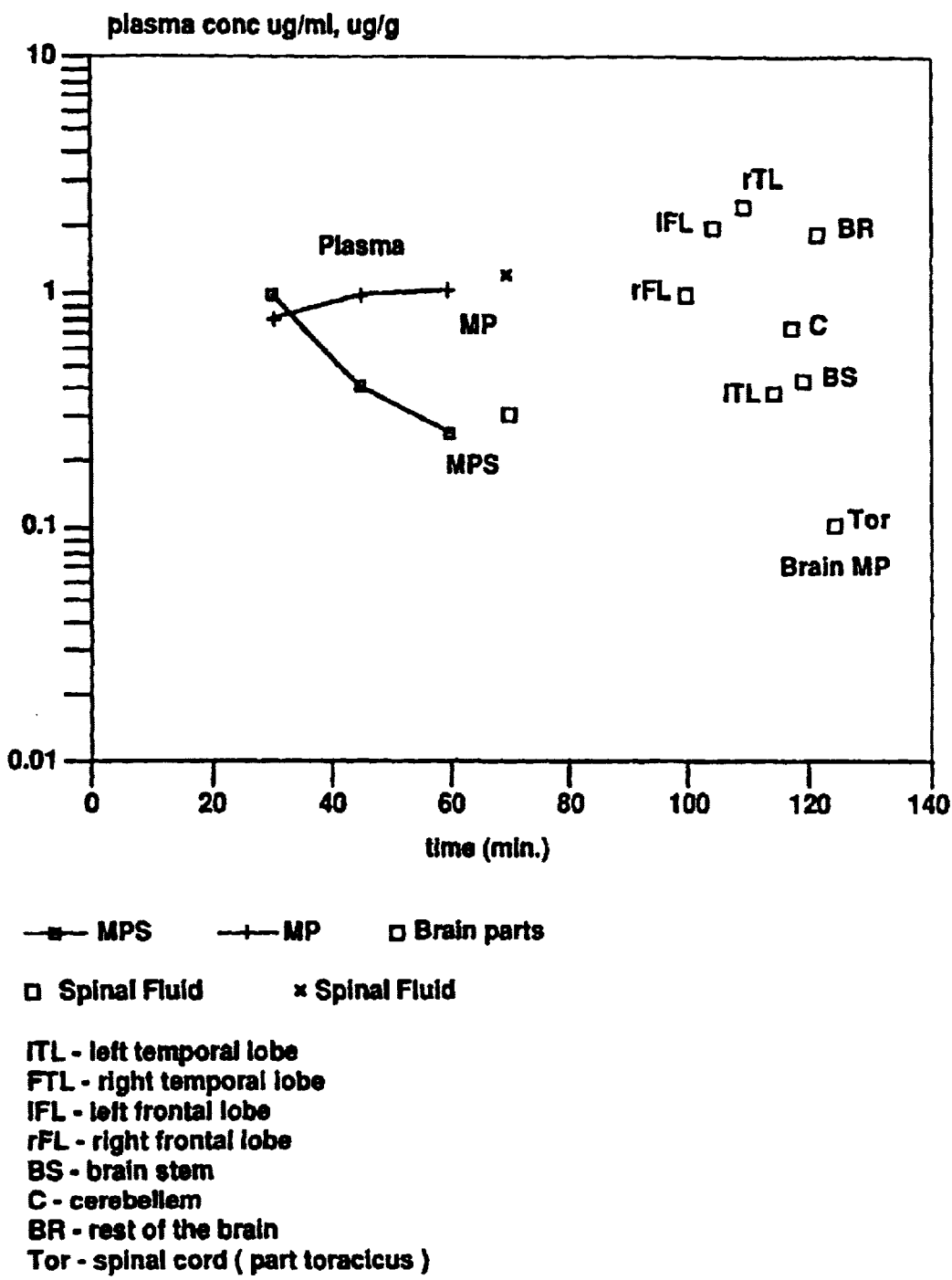
Figure 7:
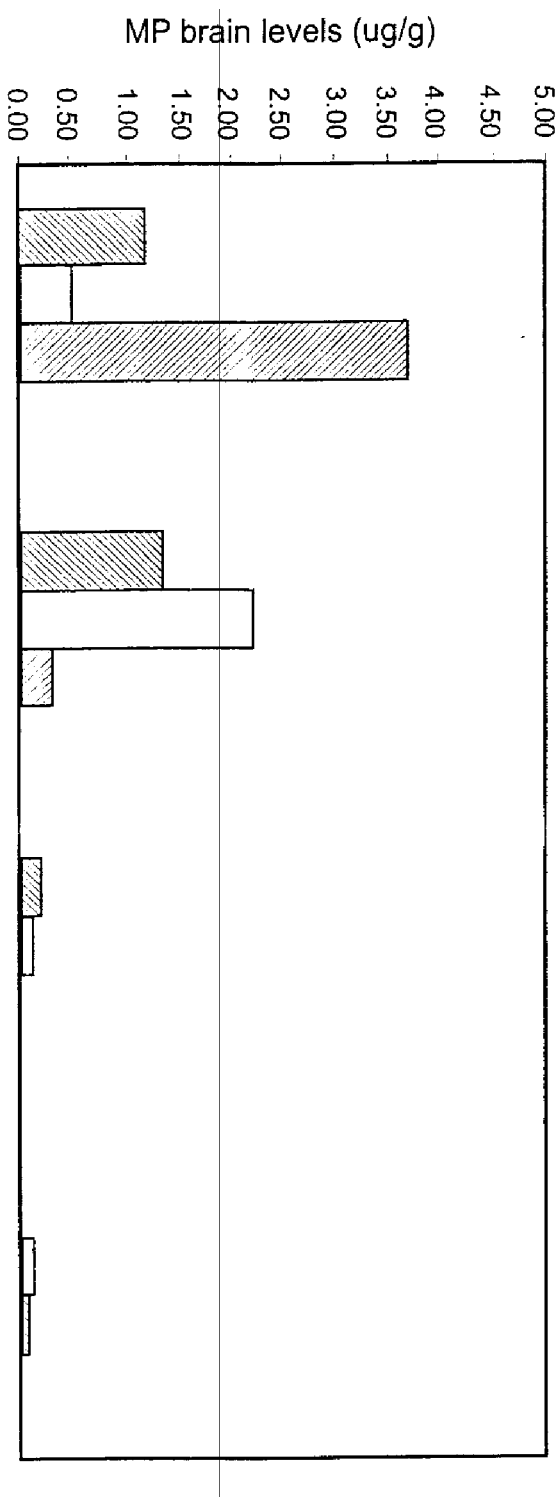

The results of the tables 5 and 6 are graphically given in FIG. 5 and FIG. 7

COMPARATIVE EXAMPLE

To show the superior results of the application of a biologically active substance according to the invention compared with the application by means of an intravenous injection, the plasma concentrations and the brain concentrations were measured in rabbits, which were treated in both ways. The following results were obtained.

TABLE 7

Plasma concentrations ($\mu$g/ml) of methylprednisolone hemisuccinate (MPS) and methylprednisolone (MP) in a rabbit after an intravenous injection of MPS 5 mg/kg and 1 mg/kg respectively.

| Time | Rabbit 4 (5 mg/kg) | | Rabbit 5 (1 mg/kg) | |
|---|---|---|---|---|
| (min.) | MPS | MP | MPS | MP |
| 0 | 0 | 0 | 0 | 0 |
| 1 | 72.91 | 12.11 | 8.79 | 1.17 |
| 2.5 | 55.19 | 13.18 | 1.77 | 0.32 |
| 5 | 14.12 | 7.98 | 0.46 | 0.30 |
| 10 | 3.47 | 5.75 | 0.22 | 0.28 |
| 15 | 1.48 | 3.97 | 0.18 | 0.25 |
| 20 | 1.13 | 3.13 | 0.14 | 0.24 |
| 25 | 0.87 | 2.95 | 0.11 | 0.23 |
| 30 | 0.67 | 2.64 | 0.10 | 0.19 |
| 40 | 0.42 | 2.00 | <0.10 | 0.16 |
| 50 | 0.28 | 1.62 | <0.10 | 0.17 |
| 60 | 0.19 | 1.38 | <0.10 | 0.16 |

TABLE 8

Brain concentrations ($\mu$g/g) of methylprednisolone hemisuccinate (MPS) and methylprednisolone (MP) in a rabbit after an MPS intravenous injection of 5 mg/kg and 1 mg/kg respectively.

| | Rabbit 4 (5 mg/kg) | | Rabbit 5 (1 mg/kg) | |
|---|---|---|---|---|
| Tissue | MPS | MP | MPS | MP |
| right frontal lobe | 0 | 0 | 0 | 0 |
| left frontal lobe | 0 | 0 | 0 | 0 |
| right temporal lobe | 0 | 0.07 | 0 | 0 |
| left temporal lobe | 0 | 0.06 | 0 | 0 |
| cerebellum | 0 | 0.06 | 0 | 0 |
| brain stem | 0 | 0.04 | 0 | 0 |
| brain rest | 0 | 0.09 | 0 | 0 |
| cervicalis spinal cord | 0 | 0.09 | 0 | 0 |
| thoracilis spinal cord | 0 | 0.08 | 0 | 0 |
| lumbalis spinal cord | 0 | 0.08 | 0 | 0 |

Figure 6:
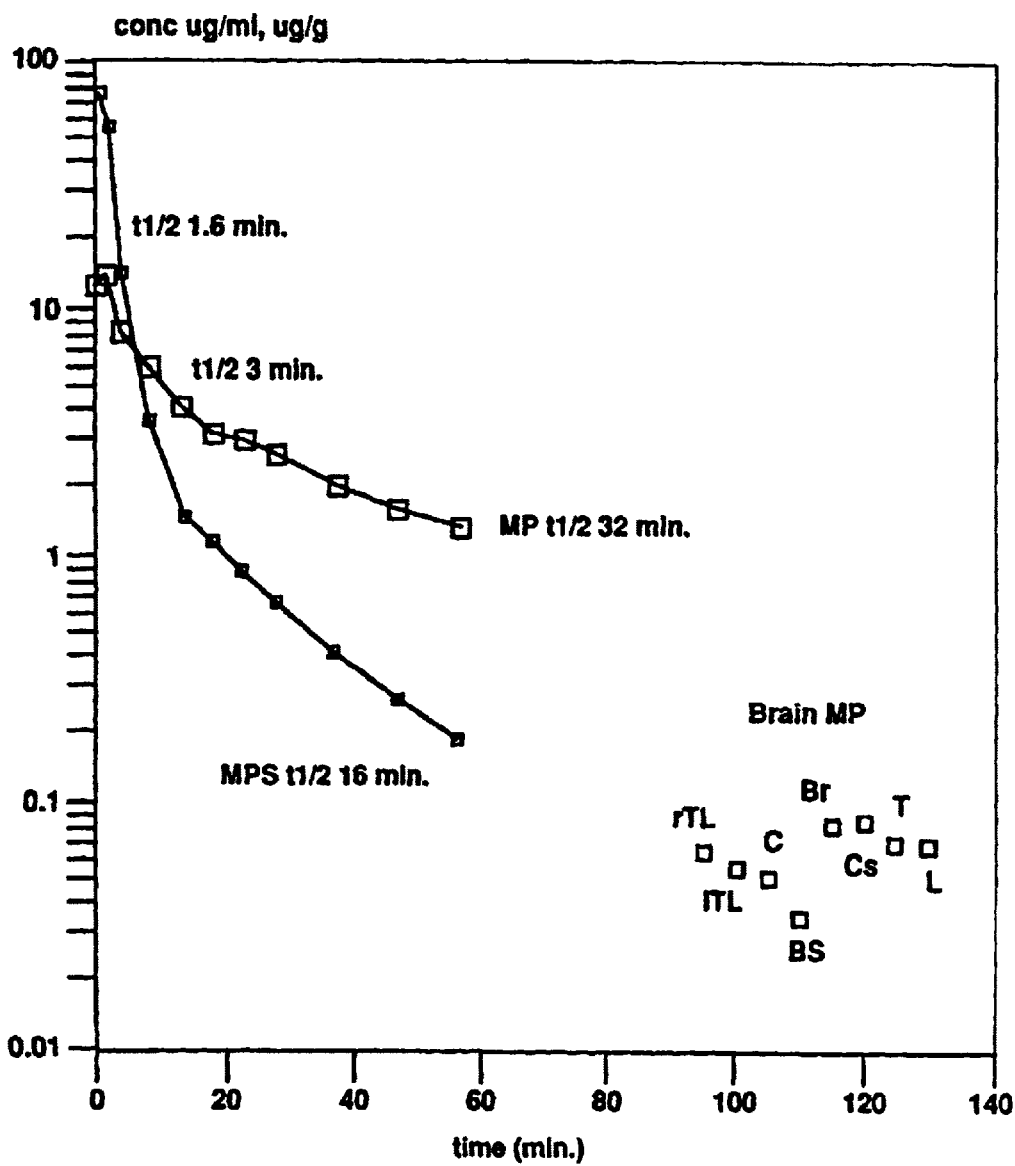
Figure 7A:
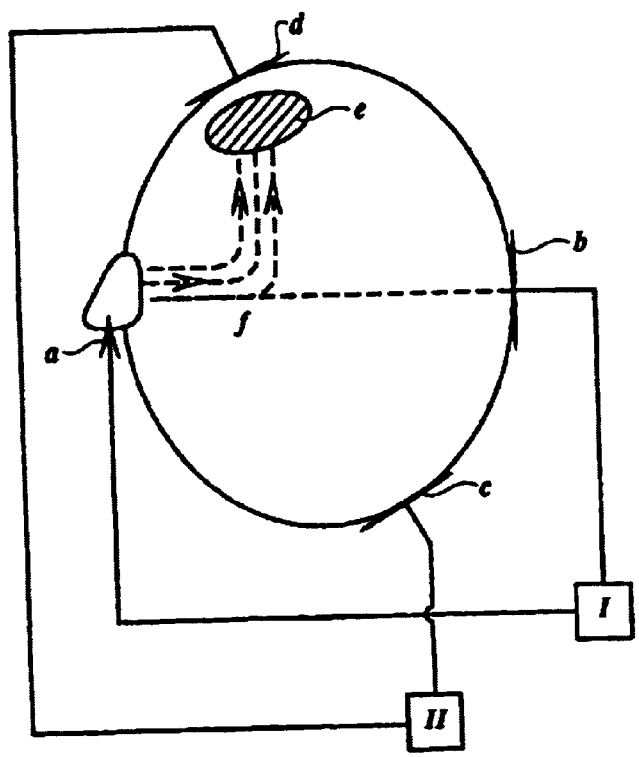
FIG. 7.—Methylprednisolone brain levels followtransnasal iontophoretic delivery and IV administration.
Figure 7B:
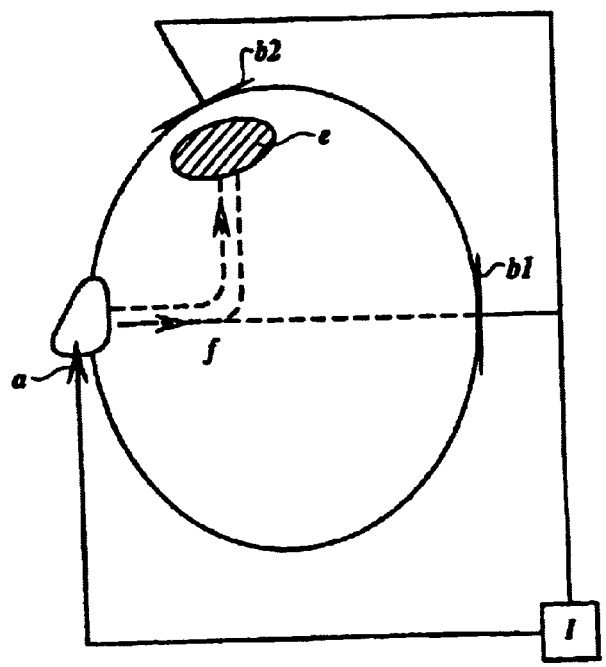

The results obtained with rabbit no. 4 are graphically given in FIG. 6 and FIG. 7.

Remark: If we compare a normal human intravenous dose of methylprednisolone hemisuccinate of 1 mg/kg, only methylprednisolone can be detected in the brain. If we give a very high dose of 5 mg/kg intravenoulsy, only methylprednisolone can be detected in the brain in a very low concentration. Contrary, if we deliver methylprednisolone hemisuccinate transnasally to the brain by means of iontophoresis as described before, the concentration of methylprednisolone in the brain is 10 to 100 times higher.

DEFINITIONS AND TERMINOLOGY

1. Biologically active compounds: This invention is useful in the delivery of directly or indirectly active substances or compounds or drugs within their broadest sense, or any other substance or compound of interest, in order to achieve a therapeutic, diagnostic or other desired, usually beneficial, effect.

Biologically active compounds, agents or substances may relate to compounds of chemical, biological or biotechnological origin; examples include organic and inorganic chemical substances, and compounds pertaining to animal, human, microbiological, plant, or viral origin.

Throughout this text the terms compounds, drug(s) and substances) are used interchangeably.

2. Blood brain barrier: The barrier separating the blood from the parenchyma of the central nervous system.

3. Cerebrospinal fluid: Abbreviation used: CSF

4. Container: any receptacle or reservoir that holds a liquid compound or a compound dissolved in a solvent or combination of these. Alternatively, the container material may form part of the matrix hat holds the biologically active compound.

What is claimed is:

1. An apparatus to enhance delivery of at least one delivery substance into the central nervous system of a mammal, utilizing the olfactory pathway(s) as a direct delivery route for the substance from an exogeneous source via the mammal's olfactory area to a target site of the mammal's central nervous system, bypassing the mammal's blood brain barrier comprising:

a tube-shaped or frusto-conical shaped first electrode sized to be located in the olfactory area of the mammal wherein the distal tip or top area of the tube-shaped or frusto-conical shaped first electrode carries a biological substance in a container, said first electrode being an active electrode constructed and arranged, shaped and sized to be non-invasively positioned in the olfactory area of the mammal at least as far as the superior nasal turbinate and having at least one perforation therein;

second electrode being a passive electrode and being constructed and arranged to be positioned on or in proximity to the head of a mammal in one or more locations, but non-invasively of the mammal, and said first and second electrodes constructed and arranged for cooperation with an energy source to establish a radiant energy gradient across at least a portion of the mammal's central nervous system; and an energy source for providing a potential gradient between said first and second electrodes so that iontophoretic delivery of the delivery substance is accomplished in a direction from said active electrode directly into one or more target sites of a mammal's central nervous system via the olfactory pathway(s) essentially bypassing the vascular system of the mammal wherein the energy source comprises an internal electrical circuit to hold a supply of energy in a rest position, prior to delivery of said at least one delivery substance, and, when said first and second electrodes are positioned in a delivery position, said internal electrical circuit activates said electrodes upon application of said electrodes to said mammal.

2. The apparatus according to claim 1 wherein the energy source comprises an electric current source with means for circuiting a supply of energy through the mammal between the electrode in a delivery position connection to said mammal and producing a current of up to 10 mA.

3. The apparatus according to either claim 1 or 2, wherein said energy source is constructed and arranged to provide a type of energy selected from the group consisting of thermal energy, an electric field, a magnetic field, high energy waves or ultrasonic waves and combinations thereof.

4. The apparatus according to claim 1 wherein said first electrode including said container holding a formulation suitable for iontophoretic delivery of the substance of interest and said first electrode together with said container is shaped to be insertable in an upper part of a nasal cavity of the mammal and constructed and arranged to make contact with nasal mucosa in an olfactory area of a mammal in order to enhance delivery of the substance of interest via said olfactory area directly into the mammal's nervous system, thereby essentially bypassing the mammal's vascular system.

5. The apparatus according to claim 4 wherein said active electrode means comprises an electroconductive base member and all but a top area of said base member is coated with an insulating material having at least one opening, and further being provided with an electroconductive material in said container supported by said top area of said base member, holding a formulation that is constructed and arranged for iontophoretic delivery of the substance of interest; said container having a form as to enable its attachment and coupling with said active electrode, the form, size and a shape of said active electrode means and its container being determined by a structure of a nasal cavity and related to its application and introduction into a nasal cavity.

6. The apparatus according to claim 5 wherein said active electrode comprises an electroconductive part having electroconductive material selected from the group consisting of stainless steel, gold, silver, titanium, copper, zinc, graphite and metal salts.

7. The apparatus according to claim 5 wherein said active electrode is formed of a polymer matrix containing an electroconductive filler material selected from the group consisting of a metal powder, powdered graphite and carbon fibers.

8. The apparatus according to any one of the claims 5–7, wherein said active electrode is provided with the container for the substance of interest, said container having a closable connection means with said top area of said active electrode.

9. The apparatus according to claim 8 wherein said container holds a self-sealing membrane that allows an in-situ refilling with a formulation containing the substance of interest, without a necessity of removal from and re-insertion into a nasal cavity.

10. The apparatus according to claim 8 wherein said container is constructed of material that is adapted to absorb, hold and release the active substance.

11. The apparatus according to claim 8 wherein said container is made of materials compatible with the formulation and with a biological environment.

12. The apparatus according to claim 8 wherein said container comprises a polymeric material consisting of hydrophilic and hydrophobic matrix structure, formed by mixing of the active substance with an inert biocompatible polymer by means of a method selected from the group consisting of melt blending, solvent coating, compression and extrusion.

13. The apparatus according to claim 12 wherein said polymeric material consisting of hydrophilic and hydrophobic matrix is cross-linked with formulation components and held in a silastic matrix.

14. The apparatus according to claim 12 wherein said inert biocompatible polymer is prefabricated and sorbed with components from a formulation containing at least one substance of interest.

15. The apparatus according to claim 1 wherein said container is made of a hydrogel that holds the delivery substance and has the structural strength to be placed in an upper part of a nasal cavity and in contact with the nasal mucosa of an olfactory area.

16. The apparatus for enhanced delivery according to claim 1, wherein said first electrode is split into two parts, one part being constructed and arranged to be fixed externally to a nose and the other part with the active substance, being constructed and arranged to be introduced into the olfactory area.

17. The apparatus according to claim 1 wherein said active electrode and passive electrode, container and an electric current source are formed as an iontophoretic assembly and the delivery substance is selected from the group consisting of amino acids, anabolics, analgesics, anesthetics, anti-adrenergic agents, antiasthmatics, anti-atherosclerotics, antibacterials, anticholesterolics, anti-coagulants, antidepressants, antidotes, anti-emetics, anti-epileptic drugs, anti-fibrinolytics, antiinflammatory agents, antihypertensives, antimetabolites, antimigraine agents, antimycotics, antinauseants, antineoplastics, anti-obesity agents, anti-Parkinson agents, antipsychotics, antirheumatics, antiseptics, antivertigo agents, antivirals, appetite stimulants, bioflavonoids, calcium channel blockers, capillary stabilizing agents, coagulants, corticosterioids, detoxifying agents for cytostatic treatment, diagnostic agents, radioisotopes, drugs for treatment of chronic alcoholism, electrolytes, enzymes, enzyme inhibitors, ferments, ferment inhibitors, gangliosides and ganglioside derivatives, hemostatics, hormones, hormone antagonists, hypnotics, immunomodulators, immunostimulants, immunosuppressants, minerals, muscle relaxants, neuromodulators, neurotransmitters, neurotropics, oligonucleotides and derivatives, osmotic diuretics, parasympatholytics, sympathomimetics, vasodilators, vasoprotectives, vectors for gene therapy, viruses, vitamins and any therapeutic agent capable of affecting a nervous system.

18. The apparatus for enhanced delivery according to any one of claim 1 or 2 wherein said apparatus is adapted to deliver at least one substance of interest from an eyelid by a transocular pathway via an optic nerve region directly into a nervous system by applying an electric field between said first electrode carried by said eyelid and a second electrode constructed and arranged for being fixed on the back of a mammal's head.

19. The apparatus according to claim 2 or 1, wherein the energy source provides an electrical current up to 10 mA.

20. The apparatus according to claim 2 or 1, wherein the energy source provides an electrical current up to 10 mA.

* * * * *

UNITED STATES PATENT AND TRADEMARK OFFICE
CERTIFICATE OF CORRECTION

PATENT NO. : 6,678,553 B2
DATED : January 13, 2004
INVENTOR(S) : Lerner

It is certified that error appears in the above-identified patent and that said Letters Patent is hereby corrected as shown below:

<u>Drawings,</u>
The sheets of drawings consisting of figures 2-7b should be deleted to appear as per attached figures 2-7b Signed and Sealed this Fourteenth Day of December, 2004

JON W. DUDAS
*Director of the United States Patent and Trademark Office*